US009839496B2

(12) United States Patent
Herrington et al.

(10) Patent No.: US 9,839,496 B2
(45) Date of Patent: Dec. 12, 2017

(54) PATIENT-SPECIFIC DENTAL PROSTHESIS AND GINGIVAL CONTOURING DEVELOPED BY PREDICTIVE MODELING

(71) Applicant: Biomet 3i, LLC, Palm Beach Gardens, FL (US)

(72) Inventors: Stephen M. Herrington, Naples, FL (US); Zachary B. Suttin, West Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 154 days.

(21) Appl. No.: 13/770,921

(22) Filed: Feb. 19, 2013

(65) Prior Publication Data

US 2014/0234801 A1 Aug. 21, 2014

(51) Int. Cl.
*A61C 5/00* (2017.01)
*A61C 13/00* (2006.01)

(52) U.S. Cl.
CPC .................. *A61C 13/0004* (2013.01)

(58) Field of Classification Search
CPC ............ A61C 5/08; A61C 5/10; A61C 9/004–9/0086; A61C 13/00–13/0021;
(Continued)

(56) References Cited

U.S. PATENT DOCUMENTS 3,732,621 A  5/1973 Bostrom
3,919,772 A  11/1975 Lenczycki
(Continued)

FOREIGN PATENT DOCUMENTS

DE  2114323  10/1971
DE  3531389  3/1987
(Continued)

OTHER PUBLICATIONS

PCT International Search Report for International Application No. PCT/US2014/014849 dated Apr. 23, 2014 (3 pages).
PCT Written Opinion for International Application No. PCT/US2014/014849 dated Apr. 23, 2014 (10 pages).
"European Application Serial No. 14753550.4, Response filed May 9, 2016 to Communication pursuant to Rules 161(1) and 162 EPC dated Oct. 28, 2015", 2 pgs.
(Continued)

*Primary Examiner* — Heidi M Eide
(74) *Attorney, Agent, or Firm* — Schwegman Lundberg & Woessner, P.A.

(57) ABSTRACT

A method of designing a patient-specific prosthesis for a current patient includes receiving scan data of a mouth of the current patient to identify conditions at a location at which the patient-specific prosthesis is to be placed on a dental implant, and determining at least two clinical factors for the current patient. The method further includes identifying a desired outcome for soft tissue for the current patient at the location, and accessing a database having soft-tissue-outcome information for each of a plurality of previous patients. The database further includes clinical-factor information for each of the plurality of previous patients. Based on the soft-tissue-outcome information and the clinical-factor information for at least one of the plurality of previous patients being related to the current patient's desired outcome and the current patient's at least two clinical factors, the method includes developing a design for the patient-specific prosthesis for the current patient.

20 Claims, 16 Drawing Sheets

(58) Field of Classification Search
CPC ......... A61C 13/08; A61C 13/20; G06F 17/50;
G06F 17/5009; G06F 17/5086; G06F
19/3437; G06F 19/321; G06F 19/322;
A61B 2019/502; A61B 2019/508; G06T
17/00; G06T 17/10; G06T 17/20; G06T
2200/08; G06T 19/00; G06T 19/20
USPC ............ 433/167, 168.1, 171–176, 191, 192,
433/199.1–202.1, 213–215; 345/419,
345/420; 700/97, 98; 382/128, 131, 132
See application file for complete search history.

(56) References Cited

U.S. PATENT DOCUMENTS

| | | |
|---|---|---|
| 3,958,471 A | 5/1976 | Muller |
| 4,011,602 A | 3/1977 | Rybicki et al. |
| 4,086,701 A | 5/1978 | Kawahara et al. |
| 4,177,562 A | 12/1979 | Miller et al. |
| 4,294,544 A | 10/1981 | Altschuler et al. |
| 4,306,862 A | 12/1981 | Knox |
| 4,341,312 A | 7/1982 | Scholer |
| 4,547,157 A | 10/1985 | Driskell |
| 4,611,288 A | 9/1986 | Duret et al. |
| 4,615,678 A | 10/1986 | Moermann et al. |
| 4,624,673 A | 11/1986 | Meyer |
| 4,663,720 A | 5/1987 | Duret et al. |
| 4,713,004 A | 12/1987 | Linkow et al. |
| 4,758,161 A | 7/1988 | Niznick |
| 4,767,331 A | 8/1988 | Hoe |
| 4,772,204 A | 9/1988 | Soderberg |
| 4,793,808 A | 12/1988 | Kirsch |
| 4,821,200 A | 4/1989 | Öberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,935,635 A | 6/1990 | O'Harra |
| 4,955,811 A | 9/1990 | Lazzara et al. |
| 4,964,770 A | 10/1990 | Steinbichler et al. |
| 4,988,297 A | 1/1991 | Lazzara et al. |
| 4,988,298 A | 1/1991 | Lazzara et al. |
| 5,000,685 A | 3/1991 | Brajnovic |
| 5,006,069 A | 4/1991 | Lazzara et al. |
| 5,015,183 A | 5/1991 | Fenick |
| 5,015,186 A | 5/1991 | Detsch |
| 5,030,096 A | 7/1991 | Hurson et al. |
| 5,035,619 A | 7/1991 | Daftary |
| 5,040,983 A | 8/1991 | Binon |
| 5,064,375 A | 11/1991 | Jörnéus |
| 5,071,351 A | 12/1991 | Green, Jr. et al. |
| 5,073,111 A | 12/1991 | Daftary |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary et al. |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,237,998 A | 8/1993 | Duret et al. |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,292,252 A | 3/1994 | Nickerson et al. |
| 5,297,963 A | 3/1994 | Dafatry |
| 5,312,254 A | 5/1994 | Rosenlicht |
| 5,316,476 A | 5/1994 | Krauser |
| 5,320,529 A | 6/1994 | Pompa |
| 5,322,436 A | 6/1994 | Horng et al. |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,343,391 A | 8/1994 | Mushabac |
| 5,344,457 A | 9/1994 | Pilliar et al. |
| 5,359,511 A | 10/1994 | Schroeder et al. |
| 5,362,234 A | 11/1994 | Salazar et al. |
| 5,362,235 A | 11/1994 | Daftary |
| 5,368,483 A | 11/1994 | Sutter et al. |
| 5,372,502 A | 12/1994 | Massen et al. |
| 5,386,292 A | 1/1995 | Massen et al. |
| 5,401,170 A | 3/1995 | Nonomura |
| 5,413,481 A | 5/1995 | Göppel et al. |
| 5,417,570 A | 5/1995 | Zuest et al. |
| 5,419,702 A | 5/1995 | Beaty et al. |
| 5,431,567 A | 7/1995 | Daftary |
| 5,437,551 A | 8/1995 | Chalifoux |
| 5,440,393 A | 8/1995 | Wenz |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,497,336 A | 3/1996 | Andersson et al. |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,556,278 A | 9/1996 | Meitner |
| 5,564,921 A | 10/1996 | Marlin |
| 5,564,924 A | 10/1996 | Kwan |
| 5,569,578 A | 10/1996 | Mushabac |
| 5,580,244 A | 12/1996 | White |
| 5,616,899 A | 4/1997 | Recigno |
| 5,651,675 A | 7/1997 | Singer |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,718,579 A | 2/1998 | Kennedy |
| 5,725,376 A | 3/1998 | Poirier |
| 5,733,123 A | 3/1998 | Blacklock et al. |
| 5,759,036 A | 6/1998 | Hinds |
| 5,768,134 A | 6/1998 | Swaelens et al. |
| 5,800,168 A | 9/1998 | Cascione et al. |
| 5,810,592 A | 9/1998 | Daftary |
| 5,813,858 A | 9/1998 | Singer |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,938,443 A | 8/1999 | Lazzara et al. |
| 5,964,591 A | 10/1999 | Beaty et al. |
| 6,008,905 A | 12/1999 | Breton et al. |
| 6,093,023 A | 7/2000 | Sala Meseguer |
| 6,120,293 A | 9/2000 | Lazzara et al. |
| 6,129,548 A | 10/2000 | Lazzara et al. |
| 6,135,773 A | 10/2000 | Lazzara |
| 6,257,890 B1 | 7/2001 | Khoury et al. |
| 6,273,720 B1 | 8/2001 | Spalten |
| 6,296,483 B1 | 10/2001 | Champleboux |
| 6,312,260 B1 | 11/2001 | Kumar et al. |
| 6,334,853 B1 | 1/2002 | Kopelman et al. |
| 6,402,707 B1 | 6/2002 | Ernst |
| 6,406,295 B1 | 6/2002 | Mahler |
| 6,558,162 B1 | 5/2003 | Porter et al. |
| 6,790,040 B2 | 9/2004 | Amber et al. |
| 6,793,491 B2 | 9/2004 | Klein et al. |

(56) References Cited

U.S. PATENT DOCUMENTS

| | | |
|---|---|---|
| 7,035,702 B2 | 4/2006 | Jelonek et al. |
| 7,059,856 B2 | 6/2006 | Marotta |
| 7,425,131 B2 | 9/2008 | Amber et al. |
| 7,551,760 B2 | 6/2009 | Scharlack et al. |
| 7,988,449 B2 | 8/2011 | Amber et al. |
| 8,185,224 B2 | 5/2012 | Powell et al. |
| 8,257,083 B2 | 9/2012 | Berckmans, III et al. |
| 8,353,703 B2 | 1/2013 | Amber et al. |
| 8,628,327 B1 * | 1/2014 | Blaisdell .............. A61C 8/0001 433/213 |
| 2001/0034010 A1 | 10/2001 | MacDougald et al. |
| 2002/0160337 A1 | 10/2002 | Klein et al. |
| 2008/0124676 A1 | 5/2008 | Marotta |
| 2008/0154419 A1 | 6/2008 | Cheng et al. |
| 2009/0087817 A1 * | 4/2009 | Jansen ................ A61C 13/0004 433/223 |
| 2009/0264894 A1 | 10/2009 | Wasielewski |
| 2010/0105011 A1 | 4/2010 | Karkar et al. |
| 2010/0240012 A1 * | 9/2010 | Lange et al. ................ 433/201.1 |
| 2010/0296710 A1 * | 11/2010 | Schneider ............ A61C 8/0001 382/128 |
| 2011/0129792 A1 | 6/2011 | Berckmans, III et al. |
| 2011/0306008 A1 | 12/2011 | Suttin et al. |
| 2012/0322025 A1 | 12/2012 | Ozawa et al. |
| 2013/0226534 A1 * | 8/2013 | Fisker .................... G06F 17/50 703/1 |

FOREIGN PATENT DOCUMENTS

| | | |
|---|---|---|
| DE | 4028855 | 3/1992 |
| EP | 0442855 | 8/1991 |
| EP | 0583829 | 2/1994 |
| EP | 0657146 | 6/1995 |
| EP | 0727193 | 8/1996 |
| EP | 0747017 | 12/1996 |
| FR | 2759896 | 8/1998 |
| GB | 1291470 | 10/1972 |
| JP | 59-151344 | 10/1984 |
| JP | 63-169115 | 11/1988 |
| JP | H05-212063 | 8/1993 |
| JP | H06-154252 | 6/1994 |
| JP | H09-218916 | 8/1997 |
| WO | 85/02337 | 6/1985 |
| WO | 94/26200 | 11/1994 |
| WO | 01/34057 | 5/2001 |

OTHER PUBLICATIONS

"International Application Serial No. PCT/US2014/014849, International Preliminary Report on Patentability dated Arp. 29, 2015", 8 pgs.

"European Application Serial No. 14753550.4, Extended European Search Report dated Feb. 3, 2017", 7 pgs.

* cited by examiner

PATIENT-SPECIFIC DENTAL PROSTHESIS AND GINGIVAL CONTOURING DEVELOPED BY PREDICTIVE MODELING

FIELD OF THE INVENTION

The present disclosure relates generally to developing the design for a dental prosthesis to be used with a dental implant.

BACKGROUND OF THE INVENTION

The dental restoration of a partially or wholly edentulous patient with artificial dentition can be accomplished through several methods involving a dental implant. One common method has two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process has sufficiently advanced, the second stage is initiated. Here, the gingival tissue is re-opened to expose an end of the dental implant. A healing component or healing abutment is fastened to the exposed end of the dental implant to allow the gingival tissue to heal therearound. The healing abutment is then removed and a prosthesis, which involves an abutment and artificial crown fitting over the abutment, is secured to the dental implant through the gingival aperture created by the healing abutment.

In an alternative method, the healing abutment can be placed on the dental implant immediately after the implant has been installed and before osseointegration. In this method, the osseointegration phase and gingival-healing step into a one-step process.

In a further alternative, the dental implant can be immediately loaded by use of a temporary prosthesis placed on the dental implant after it has been installed. In that situation, the gingival tissue heals around the temporary abutment.

Regardless of the method that is used, a primary goal is to have the soft tissue heal around the prosthesis in a predictable manner (i.e., similar to the patient's adjacent teeth) so that the prosthesis and soft tissue contours appear more natural. There are, however, many clinical factors that may impact the ability of the soft tissue to grow around and be preserved against the prosthesis, including at least the following (i) the patient's age, (ii) the patient's sex, (iii) the patient's race, (iv) the location of the implant-abutment interface relative to the bone, (v) the material of the abutment, (vi) the surface treatment on the abutment, (vii) the amount of surface area of the abutment exposed to the soft tissue, (viii) the soft-tissue displacement required when placing the prosthesis at the site after the second-phase soft-tissue healing process is complete, (ix) the type of bone at the implant installation, and (x) the patient's health conditions (e.g., smoker, diabetic, etc.).

Implant dentistry restorative methods have advanced to the digital world such that the scanning of the patient' mouth, of the impression of the patient's mouth, or the model of a patient's mouth provides the information needed for restoring the case. That information can be used to develop a patient-specific (i.e., custom) prosthesis for the patient. Some examples of the technology are discussed in U.S. Pat. Nos. 8,353,703, 8,257,083, 8,185,224, which are commonly owned and hereby incorporated by reference in their entireties. In these more modern digital dentistry systems, the creation of the design (the abutment and the crown to fit on the abutment) and the finalization of the design are generally accomplished by design technicians and dental laboratory personnel using CAD-CAM software. However, in the current systems, the designs are typically based on what the current patient requires based on his or her conditions. While the design technicians and dental laboratory personnel may rely on their experiences in designing other prostheses, the success of the soft-tissue outcome on the previously designed prostheses does not play a part in the current design.

A need exists for a patient-specific restorative system that leverages the knowledge of the soft-tissue outcomes of previous patients to develop a design for a prosthesis for a current patient. In doing so, the system provides a greater certainty that the predicted soft-tissue outcome for the current patient will become a reality for the current patient.

SUMMARY OF THE INVENTION

The present invention relates to a method of designing a patient-specific prosthesis for a current patient. The method comprises receiving scan data of a mouth of the current patient to identify conditions at a location at which the patient-specific prosthesis is to be placed on a dental implant, and determining at least two clinical factors for the current patient. The method further includes identifying a desired outcome for soft tissue for the current patient at the location, and accessing a database having soft-tissue-outcome information for each of a plurality of previous patients. The database further includes clinical-factor information for each of the plurality of previous patients. Based on the soft-tissue-outcome information and the clinical-factor information for at least a first previous patient of the plurality of previous patients being related to the current patient's desired outcome and the current patient's at least two clinical factors, the method includes developing a design for the patient-specific prosthesis for the current patient that includes design features used by an actual previous prosthesis for the first previous patient.

In an alternative embodiment, a method of designing a patient-specific prosthesis for a current patient comprises accessing a database that stores information for each of a plurality of previous patients. The information for each previous patient includes (i) clinical-factor information, (ii) prosthetic information relating to the prosthesis used on the previous patient and (iii) soft-tissue-outcome information. Based on a relationship between (i) clinical factors and desired soft-tissue outcome for the current patient and (ii) the clinical-factor information and the soft-tissue-outcome information for a first previous patient from the plurality of previous patients, the method includes selecting the prosthetic information for the first previous patient as part of a baseline design for the patient-specific prosthesis, and modifying the baseline design to develop a final design for the patient-specific prosthesis.

In a further embodiment, a method of designing a dental prosthesis for a current patient comprises identifying, within a database, a previous patient from a plurality of patients that has an actual prosthesis and an actual soft-tissue outcome that are similar to a desired soft-tissue outcome and a virtual prosthesis for a current patient. The method further includes using design features from the actual prosthesis from the identified previous patient to develop a final design for the prosthesis for the current patient.

In yet another alternative, a method of designing a dental prosthesis for a current patient comprises identifying, within a database, a subset of previous patients from a plurality of patients that had the same tooth replaced as the current patient is having, and identifying, from the subset of previous patients, a first previous patient that has an actual prosthesis that is similar to a virtual prosthesis for a current patient. The method further includes using design features from the actual prosthesis from the identified first previous patient to develop a final design for the prosthesis for the current patient.

In another alternative, the present invention is a method of designing a dental prosthesis for a current patient, comprising receiving scan data from a mouth of a current patient, and, by use of the scan data, locating a dental implant that is installed in the mouth of the current patient. The method further includes, by use of the scan data, developing a desired soft-tissue outcome and a desired prosthesis shell for the current patient. The desired prosthesis shell representing an estimated volume adjacent to the dental implant that is to be occupied by the prosthesis. The method also includes (i) identifying, within a database, a first previous patient and a second previous patient each of whom has at least two clinical conditions similar to clinical conditions of the current patient, (ii) accessing, from the database, design information for a first prosthesis used on the first previous patient and for a second prosthesis used on the second previous patient, and (iii) based on the design information and the desired prosthesis shell, developing a final design for the dental prosthesis for the current patient.

Additional aspects of the present disclosure will be apparent to those of ordinary skill in the art in view of the detailed description of various implementations, which is made with reference to the drawings, a brief description of which is provided below.

BRIEF DESCRIPTION OF THE DRAWINGS

The foregoing and other advantages of the disclosure will become apparent upon reading the following detailed description and upon reference to the drawings.

Figure 1A:
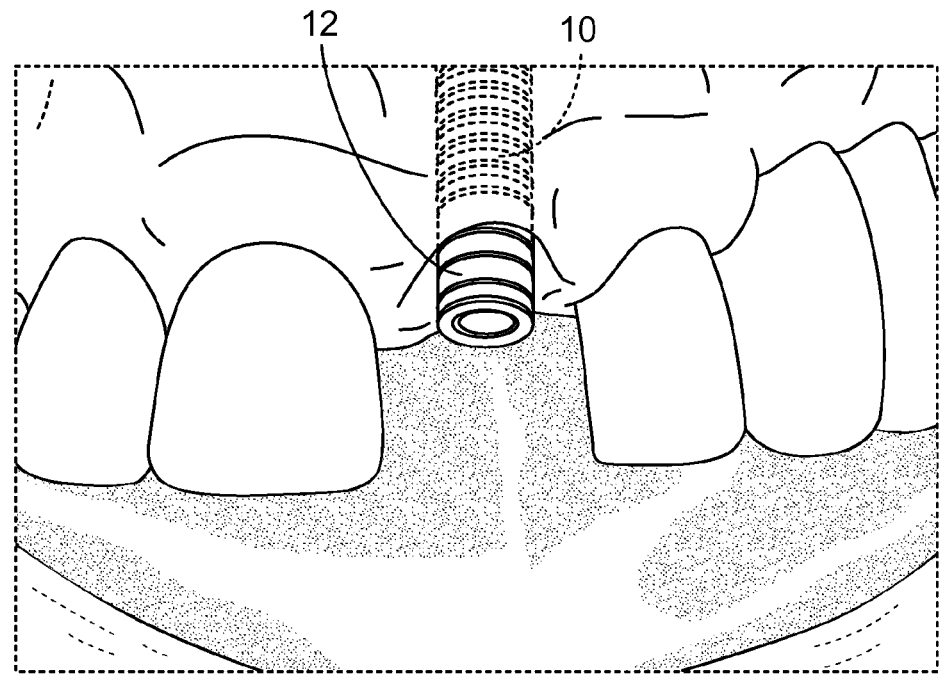
FIG. 1A is a perspective view of a current patient's mouth in which an implant has been placed to replace tooth #9 in the patient.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

Figure 1B:
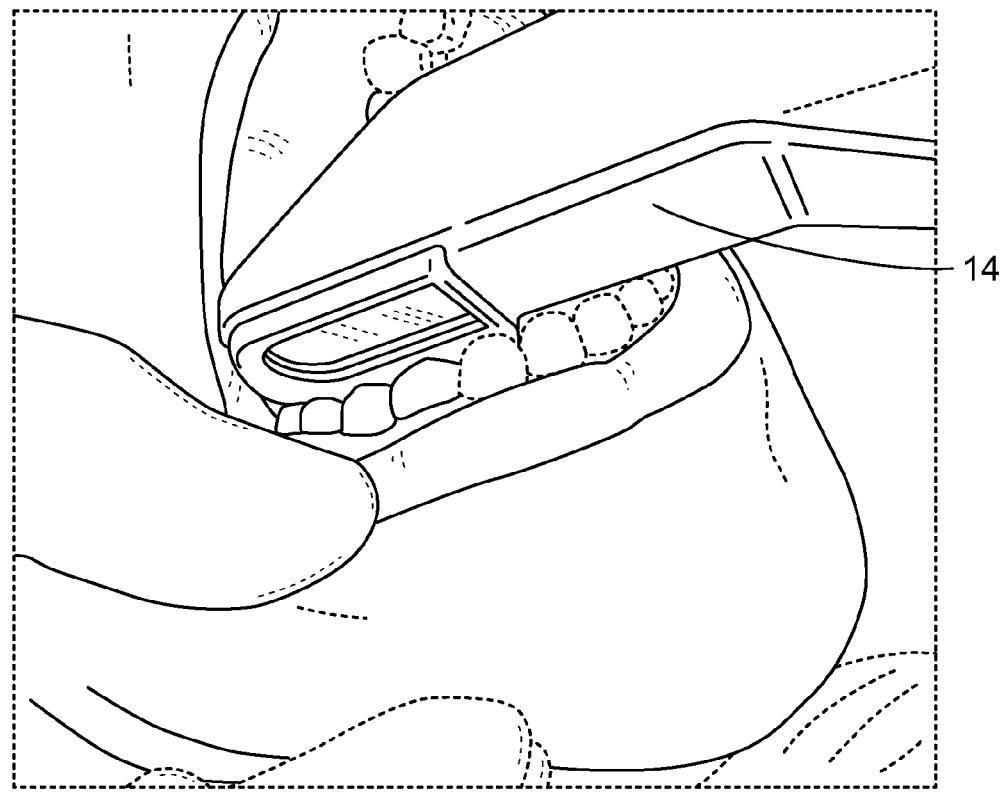
FIG. 1B is a perspective view of an intra-oral scan for locating the implant in the patient of FIG. 1A.

FIGS. 1A, 1B, 1C, and 1D illustrate steps that may be taken within a procedure for designing a patient-specific prosthesis after a dental implant 10 has been installed in the patient. In this example, the patient requires the prosthesis for tooth #9 (using the conventional tooth-numbering system), which is the location at which the implant 10 has been placed as shown in FIG. 1A. A scanning member or scanning appliance 12 may be attached on the dental implant 10 to help identify the location and angular orientation of the table of the dental implant 10, which is below the soft tissue and perhaps below the crestal bone. In FIG. 1B, an intro-oral scanner 14 is used to provide information regarding the prevailing conditions in the patient's mouth adjacent to the implant 10. The scanner 14 also scans the scanning appliance 12 so as to locate the underlying dental implant 10. While an intra-oral scanner 14 is used, the skilled artisan would understand that there are several other ways to obtain the needed information for the patient, such as CT scans of the mouth, scans of impressions of the mouth, and/or scans of dental models made from the impressions.

Figure 1C:
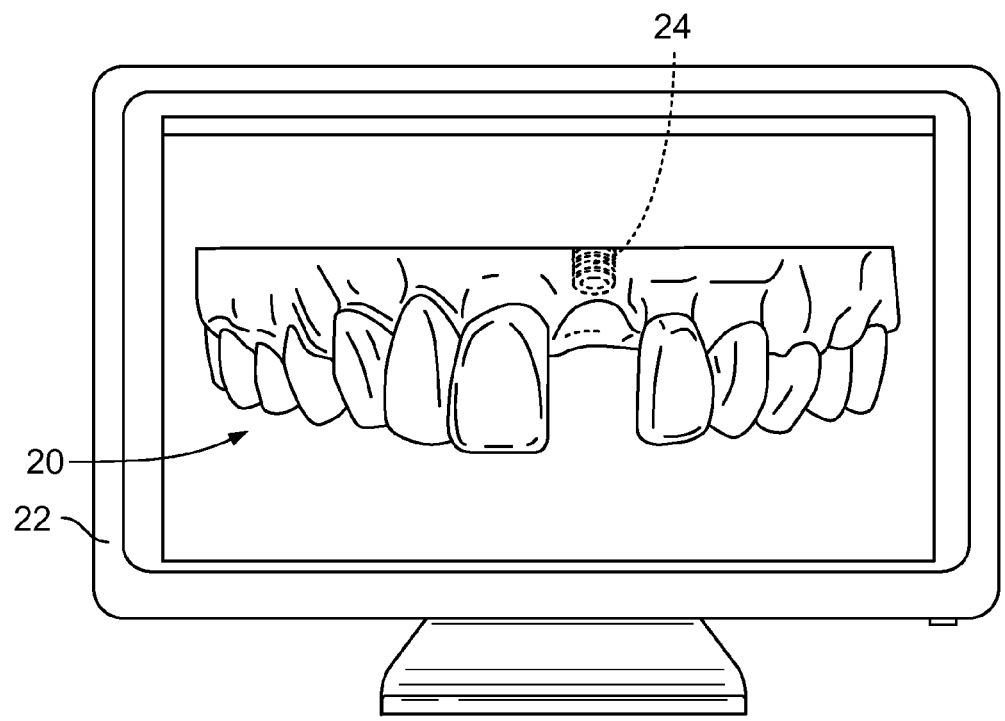
FIG. 1C is a model on a computer display that is based on the scan data obtained in FIG. 1B.

In FIG. 1C, the scan data from the scanner 14 is used to develop a virtual model 20 of patient's mouth. The virtual model 20 can then be displayed on a display monitor 22. As shown in FIG. 1C, a virtual dental implant 24 is illustrated within the virtual model 20 at a location and angular position that substantially corresponds to the location of the dental implant 10 in the patient's mouth. In other words, the scan data is also used to identify the location and angular position of the dental implant 10 in the patient's mouth, which can be accomplished through some of the processes described in U.S. Pat. Nos. 8,353,703, 8,257,083, 8,185,224, which are incorporated by reference as indicated above.

Figure 1D:
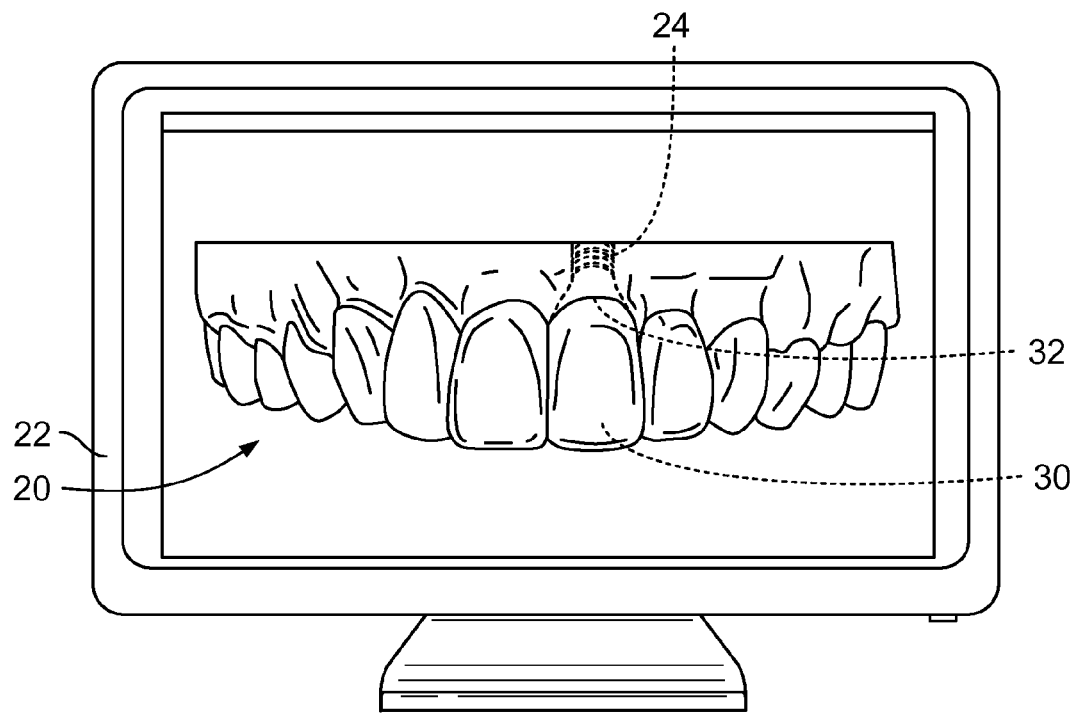
FIG. 1D is a model on a computer display that is based on the scan data obtained in FIG. 1B, and with a desired outcome for a prosthesis and the soft tissue for the current patient.

In FIG. 1D, the virtual model 20 has been modified to provide a virtual prosthesis 30 at the location where the virtual dental implant 20 is positioned within the model 20. The virtual prosthesis 30 is built from the virtual dental implant 20 and is sized and shaped to aesthetically and anatomically match the patient's adjacent teeth (i.e., tooth #8 and tooth #10) and to support the desired soft-tissue contours. The virtual prosthesis 30 at this point can be thought of as an exterior "shell" that has a desired external geometry that is substantially sized and shaped (i) to aesthetically and anatomically match and fit within the patient's adjacent teeth and (ii) to fit onto and mate with the virtual dental implant 24. The "shell" can be thought of as estimated volume that will be substantially or approximately filled by the final prosthesis. The "shell" has a sub-gingival geometry that supports the desired gingival contours and a supra-gingival geometry that provides the aesthetics of the visible portion of the tooth. The prosthesis could be monolithic, or made of multiple components. When made of multiple components, the primary support structure for the prosthesis is the abutment. The abutment fits within the "shell", mates with the implant 10, and supports a tooth-shaped crown. The tooth-shaped crown is the other part of the prosthesis. The abutment is held on the implant via screw, and the crown and abutment are typically attached via cement.

Additionally, FIG. 1D illustrates a desired soft-tissue outcome 32 for the patient over the virtual prosthesis 30. The desired soft-tissue outcome 32 is dictated by the currentpatient's existing soft-tissue contours and dimensions in the patient's mouth, and/or by what the clinician (or designer) is trying to achieve. For example, the clinician may be trying to replicate the natural tooth that is no longer there, or actually trying to improve upon the natural tooth (or teeth) that are no longer present. Some quantitative parameters related to the soft tissue (e.g., soft-tissue contour, soft-tissue height relative to the implant, and the inter-papilla fullness) are set forth below in FIGS. 8-11. Once the desired soft-tissue outcome 32 and the virtual prosthesis 30 (which is the desired size and shape of the design of prosthesis) are known, a prosthesis design system 40 (FIG. 2) then utilizes the prosthetic designs and soft-tissue outcomes from previous patients to develop (automatically or with some manual operator intervention) a prosthesis to be used for the current patient, as discussed in detail below.

Figure 2:
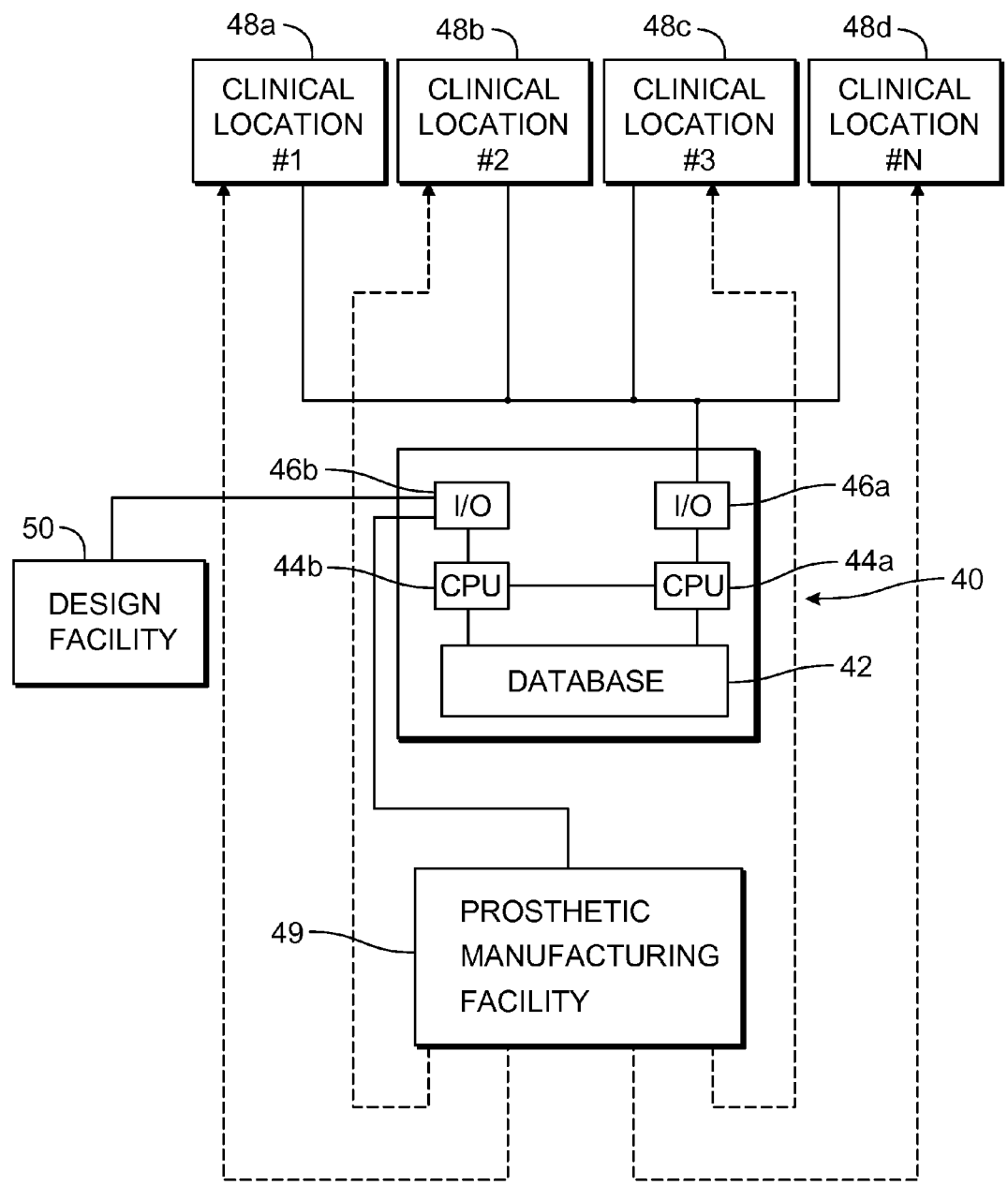
FIG. 2 is a block diagram illustrating the connection of the prosthesis design system with the clinical locations and the prosthetic manufacturing facility.

FIG. 2 illustrates one embodiment of the prosthesis design system 40 in accordance with the present invention. The prosthesis design system 40 includes at least one database 42 for storing information regarding both current patients and previous patients. It also includes one or more central processing units (CPUs) 44 for handling various functions involving the database 42. The CPU 44 may include any suitable processor(s), such as those made by Intel and AMD. By way of example, the CPU 44 may include a plurality of microprocessors including a master processor, a slave processor, and a secondary or parallel processor. The CPU 44, as used herein, comprises any combination of hardware, software, or firmware disposed in the prosthesis design system 40 that is configured to access the database 42, search the database 42, store information into the database 42, transfer information from the database 42, and communicate with external systems that are tied to the database 42. The CPU 44 may comprise one or more controllers or processors disposed proximal to one another or located in different devices or in different locations. The CPUs 44 may also be coupled to input/output (I/O) interfaces 46 that assist with communications between the prosthesis design system 40 and external systems, which include various clinical locations 48 and one or more prosthetic manufacturing facilities 49 (although only one prosthetic manufacturing facility 49 is shown).

As will be described in more detail below, the clinical locations 48 receive information concerning patients having a dental implant restored, such as the one described relative to FIGS. 1A-1D. For each patient, the information may include clinical factors associated with the patient, scanning data from scans of the patient prior to a prosthesis being attached, scanning data from scans of the patient taken shortly after (e.g., minutes, hours, days, weeks later) the prosthesis has been attached to the dental implant, and/or scanning data from scans of the patient taken long after (e.g., months or years later) the prosthesis has been attached to the dental implant. Additionally, if the modeling derived from the scan data (e.g., FIGS. 1C and 1D) is performed at the clinical location 48, the modeling information can also be transferred to the prosthesis design system 40. The information for each patient is received by the CPU 44a (via the I/O interface 46a) and stored in a record in the database 42 for that particular patient.

Information regarding the manufacturing of the prosthesis is transferred between the prosthetic manufacturing facility 49 and the prosthesis design system 40. For example, if the modeling derived from the scan data (e.g., FIGS. 1C and 1D) is performed at the clinical location 48 and already stored in the database 42, that modeling information can be transferred to the prosthetic manufacturing facility 49 where it can be used to design the specific details of the prosthesis (abutment and crown) based on previous patients' information. The abutment and crown can be manufactured once the specific details are determined. Alternatively, the modeling derived from the scan data (e.g., FIGS. 1C and 1D) can be performed at the prosthetic manufacturing facility 49 (as opposed to the clinical location 48) such that the prosthetic manufacturing facility 49 only receives scanning data from scans of the current patient prior to a prosthesis being attached. The scanning data is used to develop the models (such as those in FIGS. 1C and 1D), which are then used to design the specific details of the prosthesis (abutment and crown) based on previous patients' information, as described below. Once specific details are determined, the abutment and crown can be manufactured. If the prosthetic manufacturing facility 49 develops the models, it will transfer those specific design details back to the prosthesis design system 40 for storage with the patient's record in the database 42

Alternatively, a design facility 50 can be separate and distinct from both the prosthetic manufacturing facility 49 and the clinical location 48. The design facility 50 is linked to the prosthesis design system 40 (and can be considered a part of the prosthesis design system 40) and develops models (e.g., FIGS. 1C and 1D) from the scanning data taken at the clinical location 48. Based on the models, the specific details of the prosthesis (abutment and crown) can be designed based on previous patients' information, as discussed below. After developing the models, the design facility 50 transfers the specific details of the design back to the prosthesis design system 40 for storage with the patient's record in the database 42.

The database 42 can organize the data for the patients in various ways, as the skilled artisan would appreciate. Table I below illustrates the types of information that can be stored in the database 42 for the patients. The information in Table I relates primarily to clinical factors for each patient. However, the information stored in the database 42 for each patient will typically include information related to the (i) raw scan data from the mouth (e.g., images), (ii) the models derived and developed based on the scan data, (iii) the specific design details of the prosthesis (abutment and crown), (iv) the desired soft-tissue outcome before the prosthesis was installed, (v) the actual soft-tissue outcome after the prosthesis was installed (possibly over specified periods of time), and (vi) quantitative or qualitative indicators of whether the patient's actual soft-tissue outcome met the desired soft-tissue outcome (i.e., indicating how well the soft-tissue outcome was predicted). Some of the information will be discussed below.

needed for each patient includes the tooth number of the tooth (or teeth) being replaced. Each of the clinical factors will now be briefly discussed.

Age: While it is not necessary to exactly match a current patient's age with previous patients' ages, the age factor is intended to match the relative ages, such as within 5 years or 3 years (±5 years or ±3 years). As one example illustrating the need for the age factor, a person of age 60 is not expected to have the same type of soft-tissue outcome as a person in their 20's or 30's.

Sex: The sex factor recognizes the different anatomical sizes that generally exist between the teeth of a man and the teeth of a woman. In an alternative embodiment, the dimensions of the replaced tooth may be used to separate and distinguish sizes without the need for knowing the patient's sex.

Race: Race can be defined in various ways, such as the manner used by the U.S. Office of Management and Budget (OMB) for census purposes, which includes the categories of White (W), Black or African American (BAA), American Indian or Alaska Native (AI), Asian (AS), and Native Hawaiian or Other Pacific Islander (PI). This category is helpful because the size of the tooth being replaced, as well as the gingival tissue, may be different based on the patient's race.

Bone Type: There are four basic types of bone that can be found in the maxilla and mandible. Type I bone is very hard and dense. This type of bone has less blood supply than all of the rest of the types of bone. The blood supply is required for the bone to harden or calcify the bone next to the implant. Type II bone is not as hard as Type I. It is often preferred for certain types of placement of implants. Type III bone is less dense than Type II. Because the density is not as great as Type II, it takes more time to integrate with an implant. Type

TABLE I

Exemplary Information Stored for Patients in the Database 42.

| | | | | | Clinical Factors | | | | |
|---|---|---|---|---|---|---|---|---|---|
| Patient # | Tooth Replaced | Age | Sex | Race | Implant Location | Bone Type | Soft-Tissue Displacement | Loading Timeframe | Other Factors |
| 00001 | 6 | 45 | M | W | Sub-Crestal | I | 0 | Immediate | None |
| 00002 | 7 | 23 | F | W | Crestal | II | + | 2nd-Stage | Smoker |
| 00003 | 6 | 63 | M | BAA | Supra-Crestal | I | − | Immediate | None |
| 00004 | 9 | 44 | F | W | Sub-Crestal | II | + | 2nd-Stage | None |
| 00005 | 24 | 25 | M | AS | Sub-Crestal | II | − | 2nd-Stage | None |
| 00006 | 23 | 29 | M | PI | Crestal | III | 0 | 2nd-Stage | Diabetic |
| 00007 | 9 | 39 | M | BAA | Crestal | II | + | Immediate | None |
| 00008 | 22 | 37 | F | AS | Crestal | IV | + | 2nd-Stage | None |
| 00009 | 7 | 59 | F | AI | Crestal | I | 0 | 2nd-Stage | Smoker |
| 00010 | 10 | 34 | M | W | Supra-Crestal | I | + | 2nd-Stage | None |
| 00011 | 7 | 29 | M | W | Crestal | II | 0 | 2nd-Stage | None |
| 00012 | 9 | 41 | F | W | Sub-Crestal | II | + | 2nd-Stage | None |
| ... | ... | ... | ... | ... | ... | ... | ... | ... | ... |
| n | 23 | 65 | F | W | Sub-Crestal | III | 0 | 2nd-Stage | None |

As suggested by Table I, the patient's name is not needed. Each patient can be assigned a number or some other unique identifier that is acceptable under Health Insurance Portability and Accountability Act (HIPAA). The unique identifier allows information to be stored in association with each patient. Additionally, the other basic clinical information IV bone is the least dense of all of the bone types. Type IV bone takes the longest length of time to integrate with the implant. Bone grafting or augmentation of bone may be required often required when Type IV bone is encountered.

Implant Location: This factor considers the location of the implant's table (i.e., the top surface), which is the surface of the implant that engages the lower end of the abutment. The location of the implant's table can be sub-crestal (below the outer bone surface), crestal (substantially at the outer bone surface), or supra-crestal (above the outer bone surface). Alternatively, the implant location can be provided in a dimensional format that indicates the location of implant's table relative to the outer bone surface in terms of a dimension or ranges of dimensions (0.0 mm<"implant location below crestal bone"<0.5 mm; 0.5 mm<"implant location below crestal bone"<1.0 mm; etc.)

Soft-Tissue Displacement: Typical healing abutments are round in profile, but the artificial prostheses that eventually replace the healing abutments are not. Thus, the soft tissue may heal around the healing abutments creating a gingival emergence profile that approximated the size and contour of the healing abutment and not the size and contour of the final prosthesis that will eventually be attached to the implant. The differences between the emergence profile of the patient's soft tissue and the installed final prosthesis may require gingival tissue to be displaced, which may have an effect on the resultant aesthetics (e.g., the visual look of the patient's gingival tissue abutting the final prosthesis). Tissue displacement can be categorized in many ways. In one simplistic categorization, the amount of tissue to be displaced can be (i) positive (+) in that the prosthesis is smaller than the aperture of the healed soft tissue creating a volumetric gap between the healed soft tissue and the prosthesis into which the soft issue can move, (ii) negative (−) in that the prosthesis is larger than the aperture of the healed soft tissue and will force the soft tissue outwardly away from the prosthesis, or (iii) neutral (0) in that (+) in that the prosthesis is approximately the same size as the aperture of the healed soft tissue. Table I above uses this type of categorization for the clinical factor of soft-tissue displacement.

Alternatively, soft-tissue displacement can be represented by a more mathematical function or quantitatively. The volumetric shape of soft tissue adjacent the implant site may be known by knowing the size of the healing abutment, or by merging scans/images of the soft-tissue and hard tissue, as discussed in U.S. Publication No. 2011/0129792, which is hereby incorporated by reference in its entirety. Once this volumetric information for the soft tissue is known, then the amount soft tissue to be displaced can be calculated by knowing the prosthesis' dimensions. Or, the amount of soft-tissue displacement as a function of distance from the implant's table can be calculated, such that it may be a positive displacement in some areas and a negative displacement in other areas.

The systems and method contemplate the scanning of the soft-tissue after a healing abutment has been used. It may be that the healing abutment itself (dimensions and shape) is a clinical factor, and the system 40 conducts a search to locate previous patients that used similar (or the same) healing abutment. Thus, if the scanned image information for each of previous patients includes a scan of the gingival tissue (with or without the healing abutment) after being shaped by a healing abutment, that information may play a part in locating a previous patient with the actual soft-tissue outcome that is closest to what is desired for the current patient.

Loading Timeframe: The loading timeframe indicates whether the patient underwent the more typical two-stage implant-installation approach where the implant is "buried" under the soft-tissue and allowed to osseointegrate for a period of time. Or, the patient may have been involved in an immediate loading situation, usually with a temporary prosthesis.

Other Factors: There are other clinical factors that may influence the manner in which the patient will heal. For example, the patient's health factors (e.g. diabetic) or environmental factors (e.g. smoking) may affect the healing process.

By providing the various clinical factors, the database 42 can be easily searched to locate patients having similar clinical factors. This is advantageous when designing the prosthesis for a current patient, as discussed in the examples below. Also, it should be understood that the listed clinical factors are exemplary, and not all of the aforementioned clinical factors may needed such that the database 42 stores less information. And, it should be equally noted that other non-listed clinical factors can be included as well.

PROSTHESIS DESIGN EXAMPLE 1

In a first example, a white woman aged 43 is having tooth #9 restored by use of a dental implant and she is being treated at the clinical location 48a in FIG. 2. She is undergoing a two-stage installation method and, after the implant has been installed, scans are taken of her mouth in the region of the implant. Her clinical factor information can be inputted via a computer system at the clinical facility 48a. In this case, her implant location is "sub-crestal" and her bone type in the region of the implant is Type II. Based on the conditions and an anticipated emergence profile of a healing abutment to be used, the clinician anticipates a neutral level ("0") of soft-tissue displacement. In this example, a desired result for her soft-tissue outcome is developed at the clinical facility 48a. All of this information is then transferred to the prosthesis design system 40 of FIG. 2 and stored in the database 42.

To develop the prosthesis for the current patient, the prosthesis design system 40 locates previous patients that have similar clinical factors. Table II below provides the results of such a search that locates four previous patients (i.e., Patients Nos. 00004, 00012, 00113, and 00229) with similar clinical conditions as the current patient.

TABLE II

Initial Search Results for Prosthesis Design Example I.

| | | | | | Clinical Factors | | | | |
|---|---|---|---|---|---|---|---|---|---|
| Patient No. | Tooth Replaced | Age | Sex | Race | Implant Location | Bone Type | Soft-Tissue Displacement | Loading Timeframe | Other Factors |
| 00004 | 9 | 44 | F | W | Sub-Crestal | II | 0 | 2nd-Stage | None |
| 00012 | 9 | 41 | F | W | Sub-Crestal | II | 0 | 2nd-Stage | None |
| 00113 | 9 | 43 | F | W | Sub-Crestal | II | 0 | 2nd-Stage | None |

TABLE II-continued

Initial Search Results for Prosthesis Design Example I.

| | | | | | Clinical Factors | | | | |
|---|---|---|---|---|---|---|---|---|---|
| Patient No. | Tooth Replaced | Age | Sex | Race | Implant Location | Bone Type | Soft-Tissue Displacement | Loading Timeframe | Other Factors |
| 00229 | 9 | 45 | F | W | Sub-Crestal | II | 0 | 2nd-Stage | None |

Figure 3:
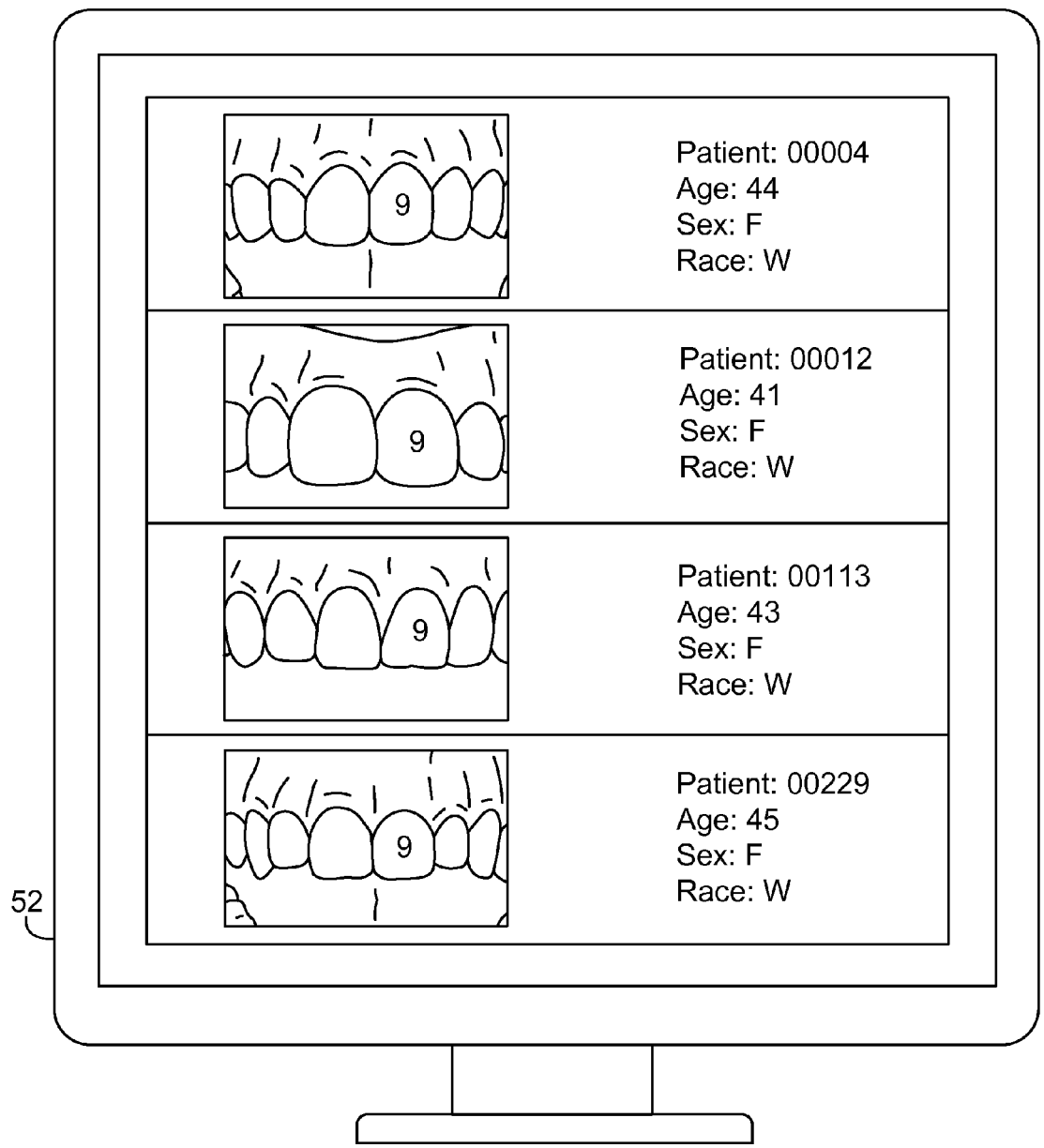
FIG. 3 is a depiction of a computer display of the actual outcomes for four previous patients who have had tooth #9 replaced.

While the four previous patients have similar clinical conditions, there can still be a wide variety of different aesthetics involved in each case. FIG. 3 illustrates the actual soft-tissue outcomes for each of the four previous patients (i.e., Patients Nos. 00004, 00012, 00113, and 00229) from Table II. In this example, an operator can use a computer display 52 associated with the design facility 50 to analyze the aesthetics associated with the actual soft tissue conditions and prostheses used by the four patients who have had tooth number 9 replaced. Based on this analysis, the operator may decide that Patient No. 00004 most closely matches the desired soft-tissue outcome of the current patient. The operator may perform this analysis by visually comparing the desired soft-tissue outcome of the current patient (FIG. 1D) to the images of each of the actual soft-tissue outcomes and prostheses of the four patients. Alternatively, the design facility 50 associated with the prosthesis design system 40 may automatically perform this function using shape-matching algorithms to determine which previous patient most closely matches the desired soft-tissue outcome of the current patient. The shape-matching algorithm may focus on the combination of (i) the desired soft-tissue outcome relative to each previous patient's actual outcome and (ii) the "shell" of the prosthesis from the current patient's model to the actual prosthesis used by each previous patient. Additionally, the location of the prosthesis relative to the gingival tissue may also play a part in determining which patient to select. After making the best selection, the design facility 50 may automatically display the best match from the previous patients on the display 52.

Figure 4:
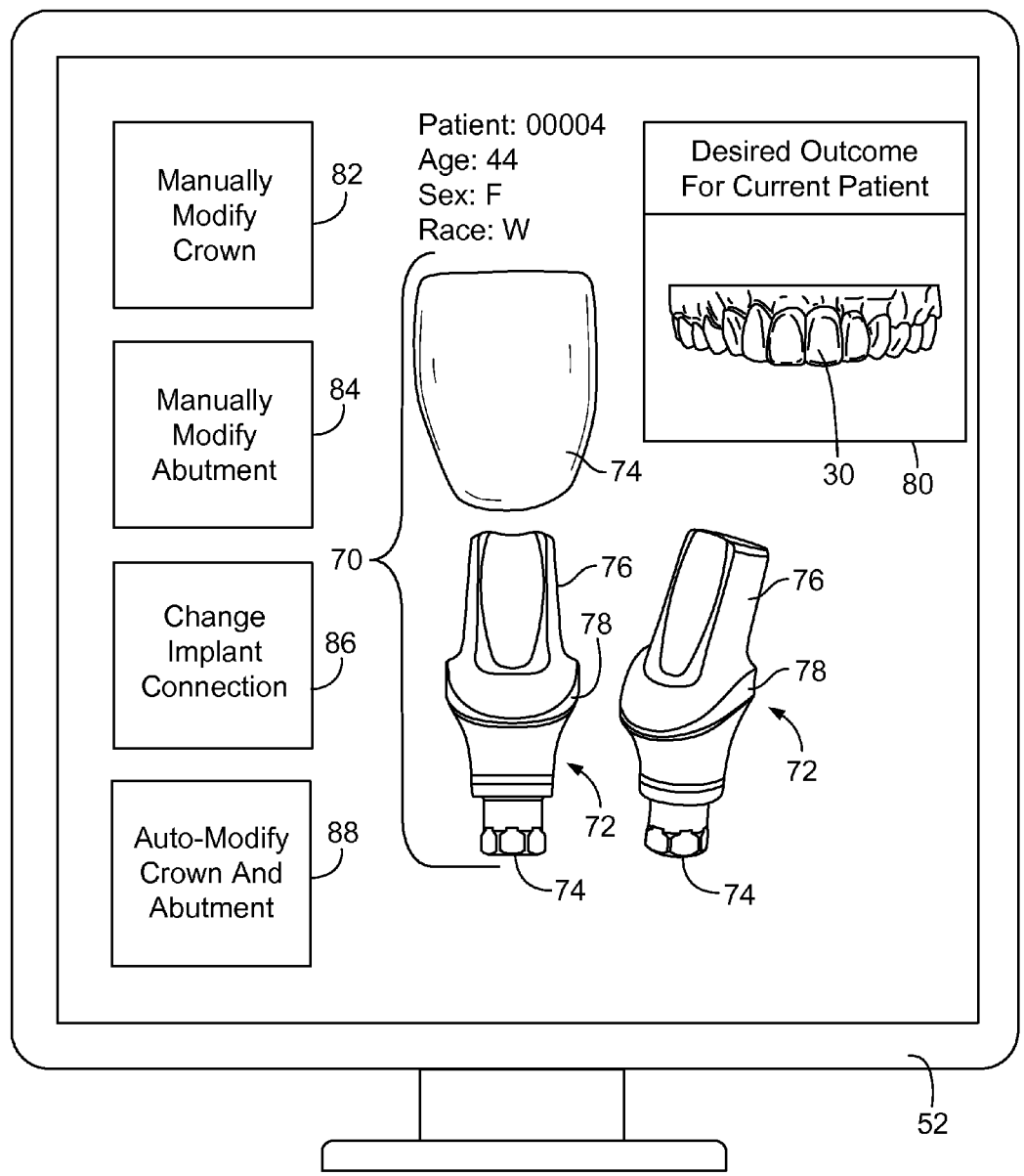
FIG. 4 is a depiction of a computer display illustrating the prosthesis for one of the previous patients of FIG. 3 and options for manipulation of the previous patient's prosthesis (abutment and/or crown) to develop a design for the current patient's prosthesis.

FIG. 4 illustrates the computer display 52 associated with the design facility 50 while an operator is designing a prosthesis 70 to be used on the current patient that is based on the prosthesis used for Patient No. 00004. The prosthesis 70 for the current patient includes an abutment 72 and a crown 74. The crown 74 is the component (for example, made of porcelain) that aesthetically matches the current patient's former tooth that is being replaced. The abutment 72 includes an implant connecting region 74 that is used for mating with the implant 10 (FIG. 1A) in the current patient's mouth so as to prohibit rotation between the abutment 72 and the implant 10. The abutment 72 also includes a post region 76 that is used for supporting the crown 74. A margin 78 on the abutment 72 represents the location at which the crown 74 meets the abutment 72.

In one embodiment that may be used in FIG. 4, the prosthesis 70 is initially displayed to the operator as the prosthesis used in Patient No. 00004. In other words, the prosthesis for the previous patient serves as a starting point for the current patient. As described above, it is the searching and matching functions associated with the prosthesis design system 40 and its database 42 that permits a previous patient's prosthesis to serve as this starting point for current patient. As shown in FIG. 4, the desired outcome for the current patient is also displayed as a model 80 on the computer display 52. Because it would be very rare for the prosthesis of a current patient to perfectly match the prosthesis used for a previous patient, the design facility 50 allows the operator to perform various design functions to modify the prosthesis 70 to best match what the current patient needs for her prosthesis. For example, it may be that only the crown 74 requires some modification such that the operator selects a first icon 82 on the computer display 52. After the first icon 82 is selected, the operator could manually modify the details of the crown 74 in the mechanical design details of the crown 74 could then be displayed on the computer display 52. Alternatively or additionally, the operator may select a second icon 84 to manually modify the abutment 72 to provide a better fitting prosthesis for the current patient. And because there are several different types of implants (in terms of their sizes and abutment mating structures), the operator may also select a third icon 86 to change the type of implant connection 74 or the size of the abutment's lower surface that is intended to engage the implant 10.

In one preferred embodiment, the operator uses inputs to alter certain aspects of the "shell" of the prosthesis for Patient No. 00004. For example, if the gingival contouring of Patient No. 00004 was very similar to what is desired for the current patient, the subgingival aspects of the "shell" of the current patient can be adjusted to be more like the subgingival aspects of the "shell" of the Patient No. 00004. And because the supra-gingival aspect of the "shell" typically has little to do with gingival contouring because it is not in contact with the soft tissue, the supra-gingival aspect of the shell of the current patient can be dictated more by the current patient's existing teeth than Patient No. 00004. In other words, the subgingival aspects of the prosthetic design for the current patient is more driven by the previous patient(s) subgingival designs, while the supra-gingival aspects of the prosthetic design for the current patient are more driven by the neighboring actual teeth of the current patient.

In yet a further alternative, the design facility 50 has a known set of design parameters and rules which provides for the automatic modification of the prosthesis used for Patient No. 00004 to design the prosthesis for the current patient. The rules and parameters would include, for example, a minimum amount of material for the post region 76 of the abutment 72 and the minimum thickness for regions of the crown 74. Thus, if the operator were to select a fourth icon 88 ("Auto-modify") on the computer display 52, a comparison would be conducted of the "shell" (exterior outline/profile) of the desired prosthesis 30 (FIG. 1D) for the current patient relative to the actual prosthesis for the previous patient, Patient No. 00004. The final design of the prosthesis 70 would automatically occur so as to develop an overall shape for the combination of the abutment 72 and the crown 74, as well as the individual shapes of both the abutment 72 and the crown 74. However, because of the searching and matching functions associated with the prosthesis design system 40 and its database 42 that led to the selection of Patient No. 00004, the automatic modification typically requires only minor or small changes to the abutment 72 and the crown 74 because the current patient's desired outcome was compared to the actual outcomes for a large number of previous patients (with similar clinical conditions) and a particular previous patient (here Patient No. 00004) was chosen because his or her actual outcome most closely matched the current patient's desired outcome.

In these embodiments, once of the final design is completed, the final design is sent to a prosthetic manufacturing facility 49 (FIG. 2) where the abutment 72 and the crown 74 are made. As indicated in FIG. 2, the prosthesis is then shipped back to the originating clinical location 48 at which the patient has been treated and it can then be attached to the dental implant. It should be noted that the prosthetic manufacturing facility 49 can be multiple facilities, one of which is associated with the manufacturing of the abutment 72 and the other of which is associated with the manufacturing of the crown 74. As one example, the prosthetic manufacturing facility 49 may be a facility within an entity that also operates the prosthesis design system 40. Or, the prosthetic manufacturing facility 49 only makes the crown 74, while the entity that operates the prosthetic design system 40 manufacturers the abutment 72. In yet a further alternative, the clinical locations 48 may have some type of manufacturing capability and provide the manufacturing of the abutment 72 and/or the crown 74.

Figure 5:
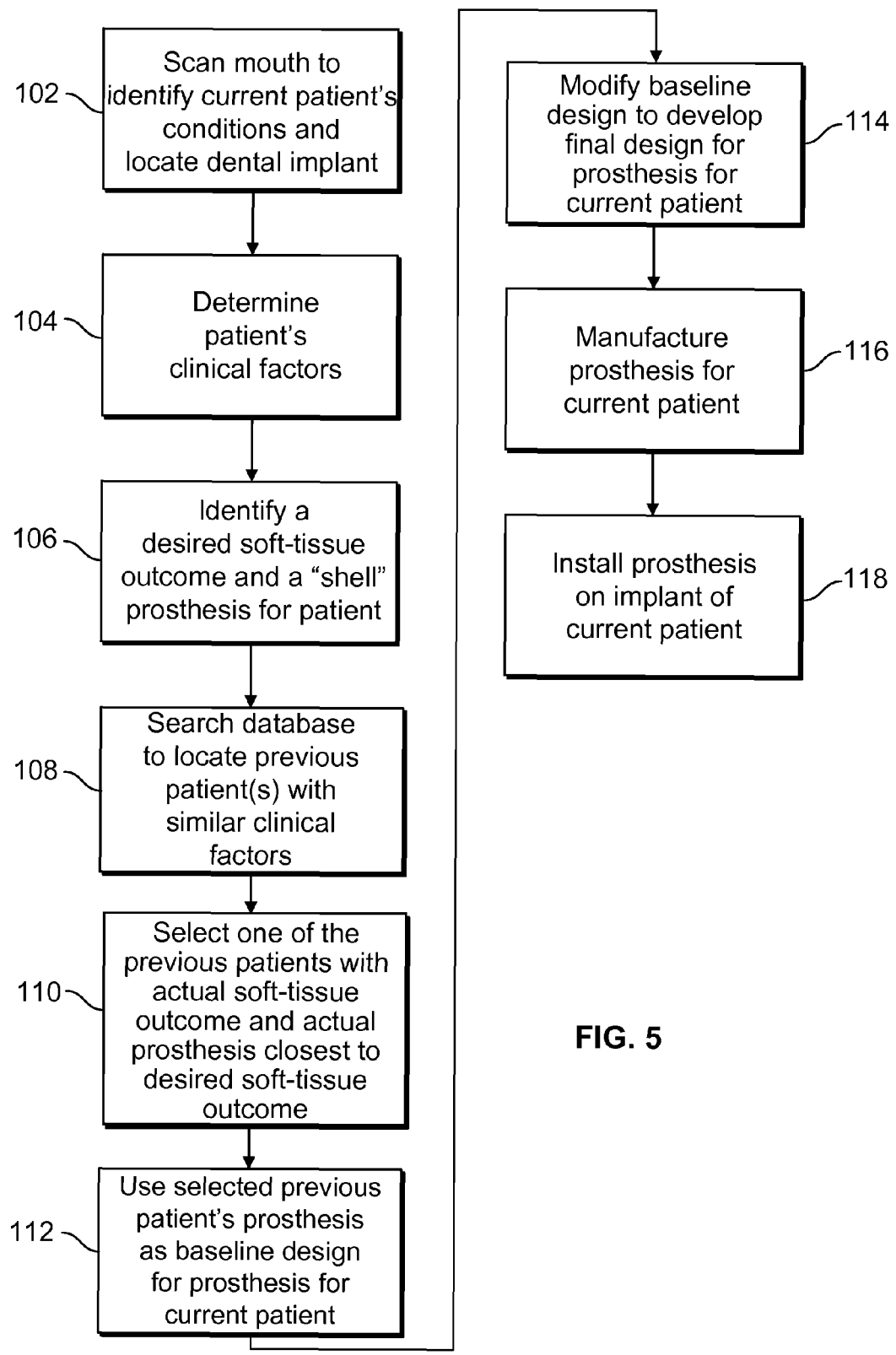
FIG. 5 is a flow chart describing one method of developing a design for the current patient's prosthesis by use of the prosthesis design system of FIG. 2.

FIG. 5 illustrates a flowchart that corresponds to a treatment methodology for the patient described above with reference to FIG. 1-4. At step 102, the mouth of the patient is scanned to help identify the patient's conditions and locate the dental implant 10. At step 104, the patient's clinical factors are determined and input via a computer input system (usually at the clinical location 48). At step 106, modeling is involved to identify a desired soft-tissue outcome 32 for the patient, and also an overall size/shape for the prosthesis (i.e., a "shell" defined by the virtual prosthesis 30). At step 108, the information involving the current patient's clinical factors is used to search the database 42 to locate previous patients with similar clinical factors.

Based on the searching at step 108, one of the previous patients is selected with an actual soft-tissue outcome and actual prosthesis that is best suited for the desired outcome for the current patient at step 110. At step 112, the prosthesis for the selected previous patient is used as the baseline design for the prosthesis for the current patient. At step 114, modifications are made to the baseline design so as to develop the final design for the prosthesis for the current patient. The final design of the prosthesis for the current patient (abutment and crown) can then be sent to the prosthetic manufacturing facility 49 (or facilities) at step 116. Once the final design has been manufactured, it can be sent to the clinical location 48 and installed on the implant 10 to the current patient at step 118.

Figure 6:
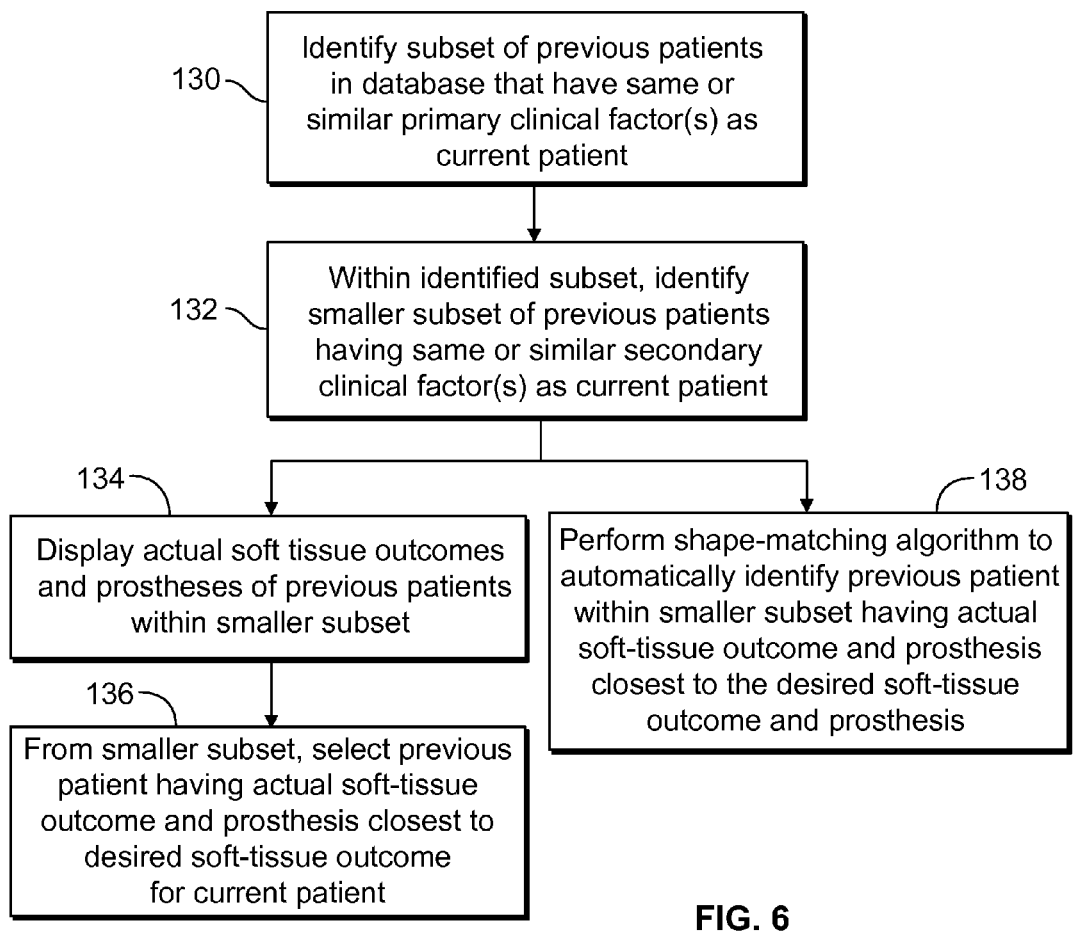
FIG. 6 is a flow chart describing one method of selecting, from a database associated with the prosthesis design of FIG. 2, a subset of previous patients that have information useful in developing a design for the current patient's prosthesis.

FIG. 6 provides details for one alternative embodiment related to the searching and selecting functions associated with steps 108 and 110 in FIG. 5. Specifically, at step 130, the database 42 is searched to identify a main subset of previous patients that have the same (or similar) primary clinical factor(s) as the current patient. A "primary" clinical factor is a factor that is critical for the design of the current patient. As an example, the tooth number that is being replaced could be considered a primary clinical factor (the patient's age, and the patient's sex could be considered primary factors as well). Next, at step 132, a smaller subset of previous patients is identified from the main subset. The smaller subset of previous patients has the same or similar secondary clinical factors as the current patient (e.g., implant location, bone type, soft-tissue displacement). Next, consistent with FIG. 3, the actual soft-tissue outcomes and prosthesis of the previous patients within the smaller subset is displayed at step 134. At step 136, one of the previous patients having an actual-soft-tissue outcome and prosthesis that is closest to the desired soft-tissue outcome and prosthesis for the current patient is then selected.

Alternatively, instead of operator interaction and selection at steps 134 and 136, the method can use a shape-matching algorithm to identify one of the previous patients within the smaller subset at step 138. After identifying the previous patient with the actual soft-tissue outcome and actual prosthesis that is the closest to the desired soft-tissue outcome for the current patient, an operator can then begin to modify the baseline design of the prosthesis for the identified previous patient to better fit the current patient.

The methods discussed with respect to the present invention have employed a dual comparison in which the shapes and dimensions of the actual and desired soft-tissue outcomes represent a first comparison, and the overall shape and profile of the actual and desired (i.e., from the model) prostheses represent a second comparison. In such and embodiment, once previous patients in the database 42 have been identified as having actual soft-tissue outcomes that are relatively close to the current patient, then a secondary comparison can be performed on those identified previous patients to determine which one used a prosthesis that is closest in its overall profile to the desired prosthesis (i.e., the "shell" prosthesis disclosed in the model of FIG. 1D).

Alternatively, because the shape and dimensions of the actual soft-tissue outcome of the previous patient are relatively close to (i.e., there is some relationship between them) the desired shape and dimensions of the soft tissue of the current patient, there is a presumption that the prostheses between the two patients should be relatively close as well. In this situation, only the actual and desired soft-tissue outcomes are compared to identify a previous patient who has an actual soft-tissue outcome that is the closest to the desired soft-tissue outcome. That previous patient's prosthesis (abutment and crown) is then used as the starting point for the current patient's prosthesis.

Figure 7:
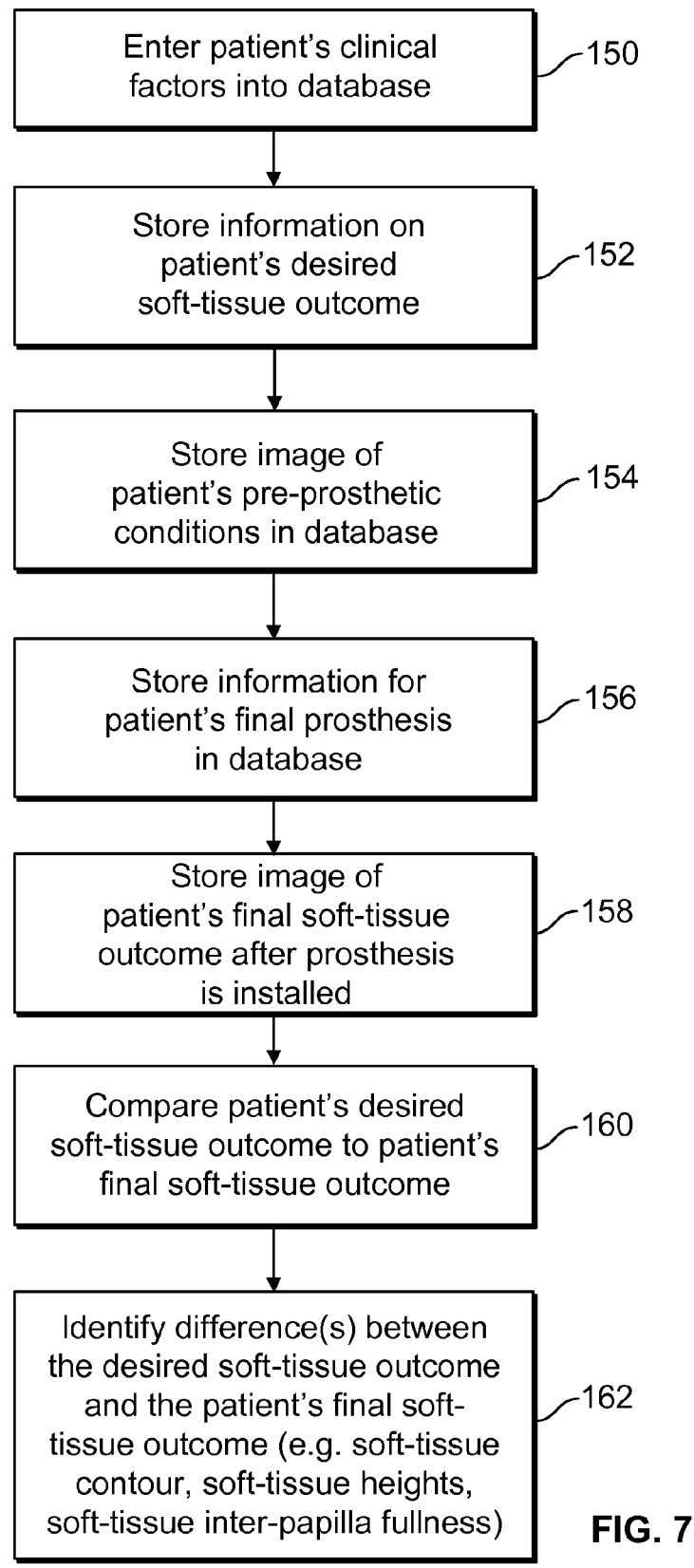
FIG. 7 is a flow chart describing one method of entering a patient's clinical factors, desired soft-tissue outcome, and actual soft-tissue outcome in the database associated with the prosthesis design of FIG. 2.

FIG. 7 illustrates a flowchart by which a patient's information (including a patient identifier) is entered and stored into the database 42, although the ordering of the steps is not critical. At step 150, the patient's clinical factors are entered and stored into the database 42. At step 152, information related to the patient's desired soft-tissue outcome 32 (e.g., FIG. 1D) from the modeling is stored in the database 42 as well. The images related to the patient's pre-prosthetic conditions are also stored in the database 42 at step 154. The final design for the patient's prosthesis is stored in accordance with step 156.

After the prosthesis has been installed on the implant, an image can be stored of the patient's final soft-tissue outcome at step 158. It should be noted, however, that multiple images after the installation of the prosthesis on the implant can be taken over a period of time because the dimensions and shape of the soft tissue along the prosthesis may change. At some point in time (preferably when the patient's soft tissue has reached a steady-state condition), a comparison is taken between the patient's desired soft-tissue outcome in the patient's actual soft-tissue outcome at step 160. This comparison determines how accurate a patient's soft-tissue outcome can be predicted. Preferably, the comparison focuses on certain soft-tissue parameters so as to identify differences between the desired soft-tissue outcome and the patient's actual soft-tissue outcome, as indicated in step 162. The soft tissue parameters may include for example the soft tissue contour, the soft tissue height, and the soft tissue inter-papillae fullness, which are described below with reference to FIG. 8-11.

Figure 8:
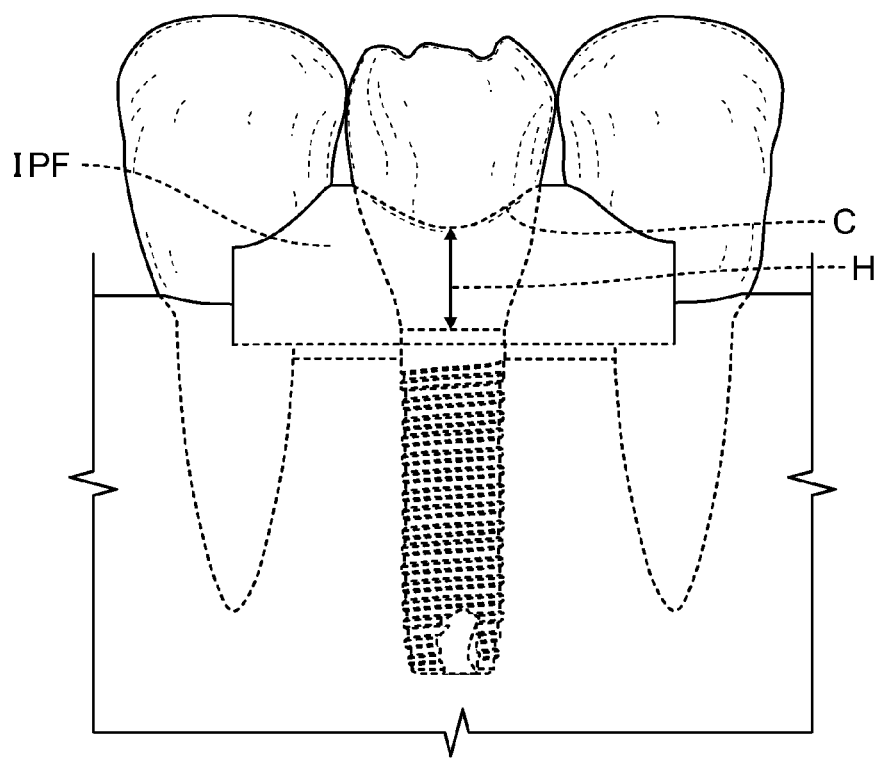
FIG. 8 is an illustration of a soft-tissue outcome and prosthesis with the factors of soft-tissue contour, soft-tissue height, and soft-tissue inter-papilla fullness displayed.

FIG. 8 illustrates three parameters that can be used to describe features of the soft tissue of the patient. The soft-tissue contour "C" represents the curvature of the line at which the soft tissue meets the prosthesis. The soft tissue height "H" represents the height or dimension measured between the table of the implant and the mid-facial region of the soft-tissue contour "C". The inter-papillae fullness "IPF" represents the volume of soft tissue at locations on one side or both sides of the prosthesis, and can be evaluated by a cross-section taken into the plane of the paper of FIG. 8.

Figure 9A:
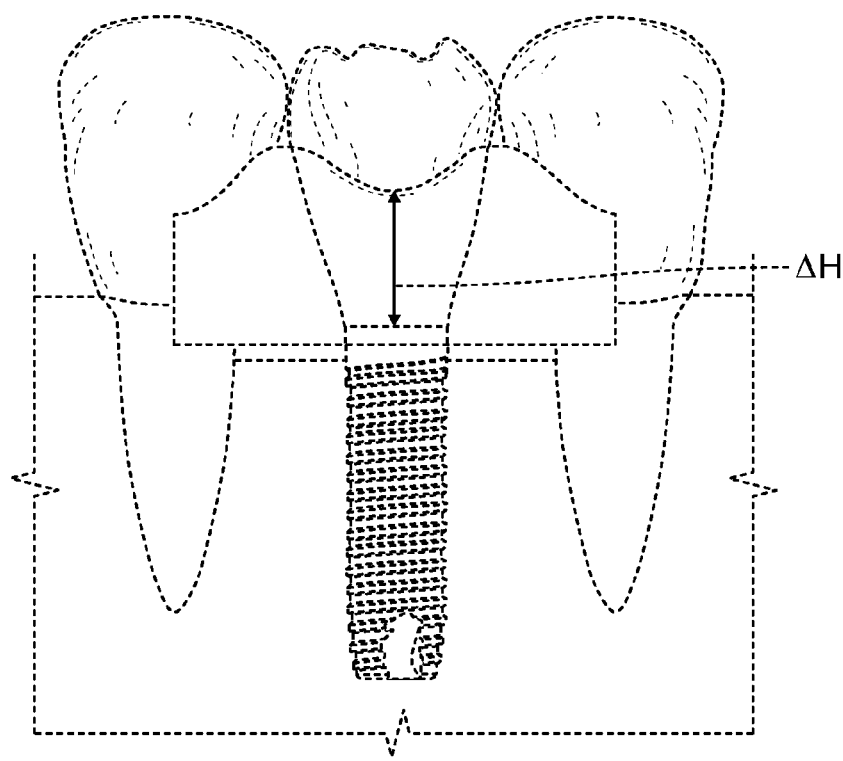
FIG. 9A is a first illustration of a different soft-tissue outcome in that the soft-tissue height is different relative to FIG. 8.
Figure 9B:
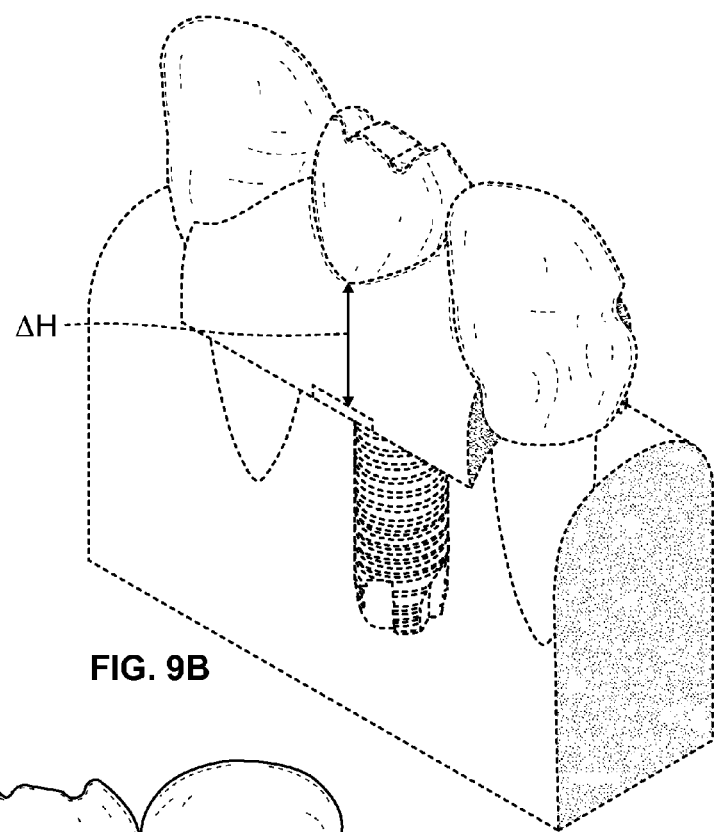
FIG. 9B is a second illustration of a different soft-tissue outcome in that the soft-tissue height is different relative to FIG. 8.

Assuming FIG. 8 illustrates a desired soft-tissue outcome for a patient, FIGS. 9A and 9B illustrate an actual outcome in which the soft-tissue height "H" increased relative to what was desired in FIG. 8. This change in the soft-tissue height ("ΔH") would suggest that at least one parameter in the patient's soft-tissue outcome was not accurately predicted.

Figure 10A:
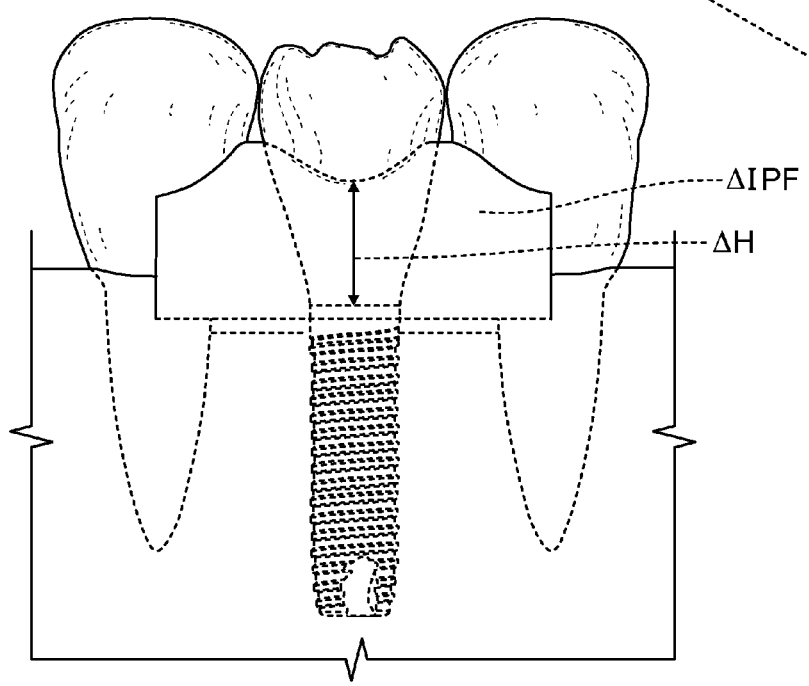
FIG. 10A is a first illustration of a different soft-tissue outcome in that the soft-tissue height and the soft-tissue inter-papilla fullness are different relative to FIG. 8.
Figure 10B:
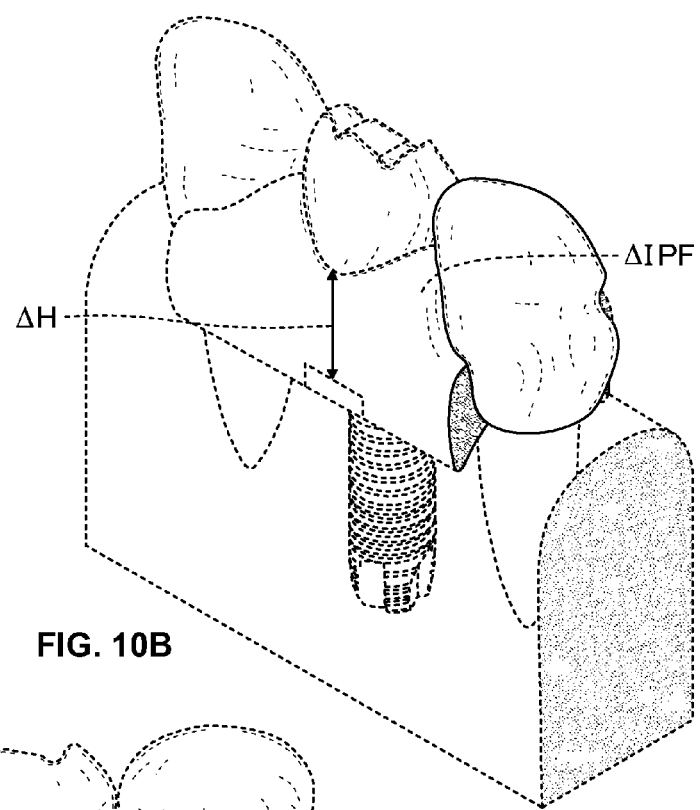
FIG. 10B is a second illustration of a different soft-tissue outcome in that the soft-tissue height and the soft-tissue inter-papilla fullness are different relative to FIG. 8.

Again, assuming FIG. 8 illustrates the desired soft-tissue outcome for a patient, FIGS. 10A-10B represent a different actual outcome in which both the soft-tissue height "H" and the inter-papillae fullness "IPF" were not predicted. In this instance, the patient actually experienced more soft-tissue growth and attachment along the height of the prosthesis ("ΔH") and more fullness of the soft tissue between the prosthesis and the adjacent tooth ("ΔIPF"). On the other hand, the soft tissue contour "C" was predicted (i.e., it is substantially close to the desired contour "C" from the desired soft-tissue outcome).

Figure 11:
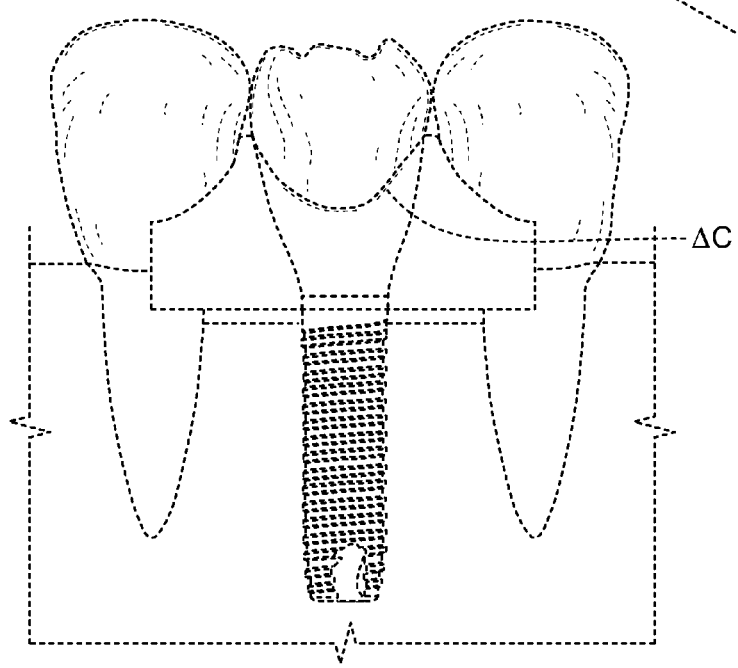
FIG. 11 is an illustration of a different soft-tissue outcome in that the soft-tissue contour is different relative to FIG. 8.

Assuming FIG. 8 illustrates the desired soft-tissue outcome for a patient, FIG. 11 represents a situation in which the actual outcome was substantially predicted with respect to the soft tissue height "H" and the inter-papillae of fullness "IPF", but the soft-tissue contour was not predicted ("ΔC"). In all of the comparisons, it should be understood that having a perfect prediction is very unlikely and finding the desired outcome to be substantially close to the predicted outcome is acceptable.

The benefit of recording the comparisons between the desired soft-tissue outcome and the actual soft-tissue outcome is that trends can be seen in the clinical data acquired from the previous patients and used to augment or enhance the design of the prosthesis for current patients. Because the soft tissue growth and attachment along the sides of prosthesis can relate to many factors, these trends can help to develop designs for specific teeth that are being replaced or for specific types of patients. In other words, what works well on tooth number 9 may not work well for tooth number 12. Or, what may work well for a 65-year-old male may not work well for a 23-year-old female.

PROSTHESIS DESIGN EXAMPLE 2

This Example 2 is similar to Prosthesis Design Example 1. However, additional prosthetic-based clinical factors and predicted soft-tissue outcomes are analyzed from previous patients to arrive at the final design for the current patient. And, the design process is more automated and requires less (or no) manual operator inputs or evaluations.

In Prosthesis Design Example 2, while Patient No. 00004 had the closest actual outcome relative to the desired outcome for the current patient, the data from patient number 00004 related to the prediction in the actual soft-tissue outcome was not entirely accurate. Specifically, for Patient No. 00004, the actual soft tissue height "H" did not match the desired soft tissue height, such as the outcome shown in FIGS. 9A-9B.

Accordingly, the database 42 can be used to locate prosthetic-based clinical factors for previous patients that led to more predictable soft-tissue outcomes. Table III is similar to Table II above in that previous patients have been identified as having potentially beneficial information for the design of the current patient based on their clinical factors (e.g., tooth number, age, sex, race). However, Table III includes ten previous patients along with their prosthetic-based clinical factors and information related to how well the soft-tissue outcome for each of the previous patients was predicted.

TABLE III

Search Results for Prosthesis Design Example 2

| Pat. No. | Implant Location | Prosthetic-Based Clinical Factors | | | Actual Outcome v. Desired Outcome | | |
|---|---|---|---|---|---|---|---|
| | | Abutment Material | Platform Switch | Abutment Micro-Structure | Predicted Soft-Tissue Contour | Predicted Soft-Tissue Height | Predicted Inter-Papilla Fullness |
| 00004 | Sub-Crestal | ZrO2 | Y | N | Y | N | Y |
| 00012 | Crestal | Ti | Y | N | Y | Y | N |
| 00113 | Crestal | ZrO2 | Y | Y | N | Y | N |
| 00229 | Crestal | Ti | N | N | Y | N | N |
| 00301 | Sub-Crestal | ZrO2 | N | Y | Y | N | Y |
| 00389 | Sub-Crestal | ZrO2 | N | Y | Y | Y | Y |
| 01021 | Crestal | Ti | Y | Y | N | N | Y |
| 01115 | Crestal | ZrO2 | Y | N | Y | N | N |
| 01418 | Crestal | Ti | Y | Y | Y | Y | Y |
| 01492 | Sub-Crestal | ZrO2 | N | Y | Y | Y | Y |

In Table III, the desired soft-tissue outcome and prosthesis for the current patient most closely matches the actual soft-tissue outcome and prosthesis of previous Patient No. 00004. However, for Patient No. 00004, her actual soft-tissue outcome did not exactly match her desired soft-tissue outcome. As noted in the 7th column, the Predicted Soft-Tissue Height was not met.

On the other hand, two other previous patients—Patients No. 00389 and 01492—may have had prosthetic geometries that did not match as well to the current patient as Patient No. 00004. But, the Predicted Soft-Tissue Contour, Predicted Soft-Tissue Height, and Predicted Inter Papilla Fullness were met, as noted by the fact that those two previous patients' desired soft-tissue outcome and their actual soft-tissue outcomes were substantially the same. However, for previous Patients Nos. 00389 and 01492, the abutment characteristics (e.g., sub-gingival features of the prosthesis) were different because neither was "Platform Switched" and both had a type of "Abutment Micro-Structure" that is designed to help hold the soft tissue along the side of the prosthesis.

Accordingly, based on the data from the previous patient Nos. 00004, 00389 and 01492, the prosthesis design system 40 may automatically develop a design for the current patient's prosthesis. The design has a geometry similar to patient No. 00004, except that it is not Platform Switched (i.e., its base has the same diameter as the table of the implant). And, its outer surface that is intended to engage the soft-tissue has the same type of Abutment Micro-Structure as Previous Patient Nos. 00389 and 01492.

Figure 12:
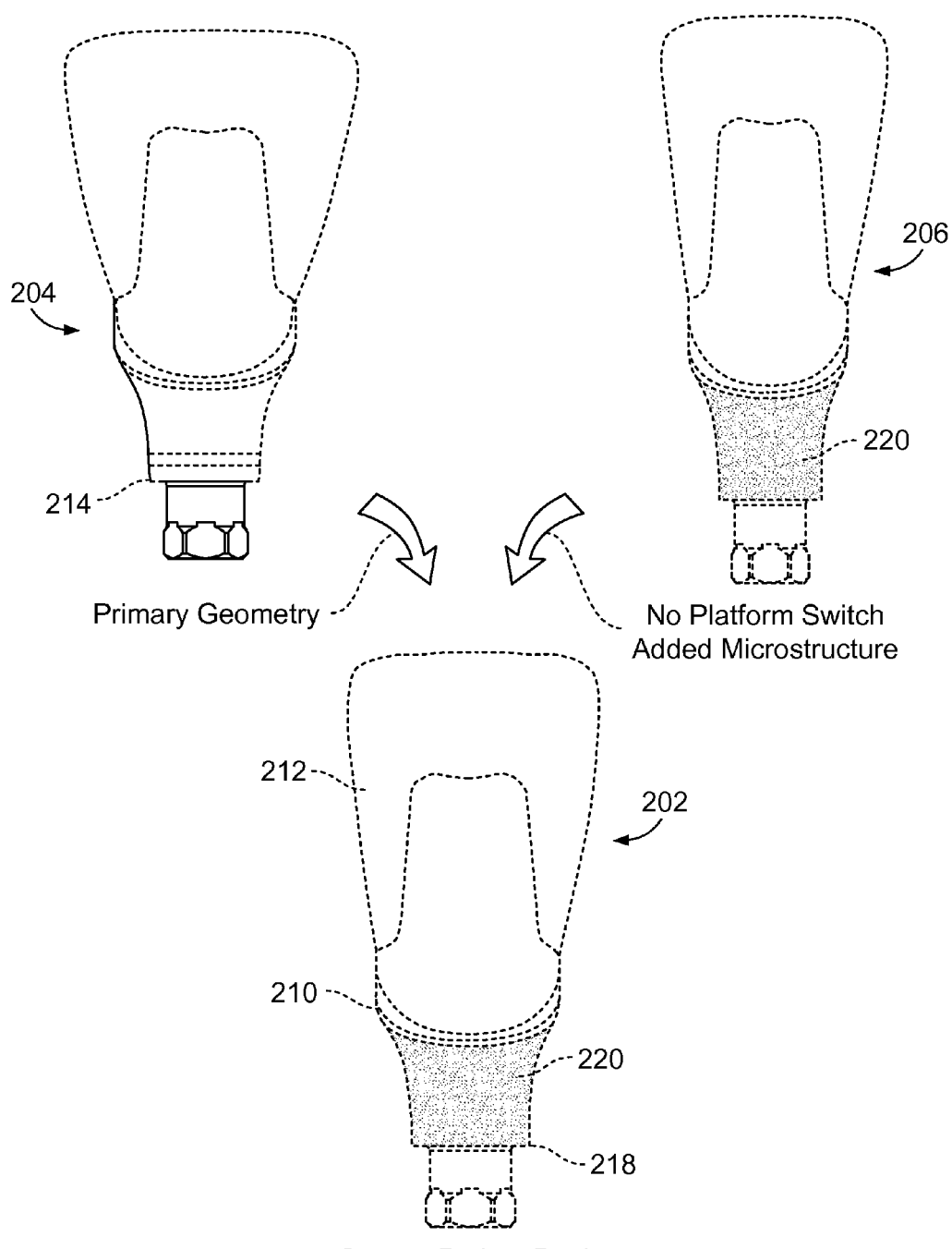
FIG. 12 graphically illustrates the development of a current patient's prosthesis by merging of design features from two prostheses used by two previous patients, as described relative to Table III.

FIG. 12 graphically illustrates the development of a design for the current patient's prosthesis 202 by merging of design features from the prosthesis 204 of Patient No. 00004 and the prosthesis 206 of Patient No. 00389 (the prosthesis for Patient No. 01492 has the same features as Patient No. 00389 and, thus, is not shown). The prosthesis 202 for the current patient will be include a zirconia oxide (ZrO2) abutment 210 (as opposed to Titanium "Ti" material) and a crown 212. The abutment for the prosthesis 204 is platform switched, which in this case is noted by a lower beveled edge 214. On the other hand the abutment for the prosthesis 206 is not platform switched, and in this case lacks a lower beveled edge. Because the design for the current patient is to lack the "platform switching" feature, the lower edge 218 of the abutment 210 is not beveled. Skilled artisans will understand that "platform switching" is associated with the geometric relationship between the abutting surface of the abutment and the implant table. If the abutting surface of the abutment is smaller than the implant table, the implant-abutment relationship is said to be "platform switched." Hence, FIG. 12 is merely for illustrating the merging of two previous patients' prosthetic designs. The platform switching feature can include a beveled lower edge on the abutment, as long as the size of the implant's table is slightly larger than the beveled edge.

FIG. 12 also shows that the abutment 210 in the prosthesis 202 for the current patient includes the same microstructure 220 as the abutment of prosthesis 206 is associated with Patient No. 00389. The microstructure 220 can be one of a variety of structures, such as an acid etched surface, a machined microgroove surface, a laser-etched microgroove surface. Alternatively, an additive feature, such as a protein or a salt, may be added to the surface of the abutment to create the microstructure. It should also be known that the microstructure may further include alternatively or additionally various types of nanostructures that may help to enhance the attachment of the soft tissue along the surface of the prosthesis 202. And, the database 42 can be populated to indicate the type of microstructure used on the abutment for each patient, so as to help identify which types of microstructures work best in certain situations for patients.

Figure 13:
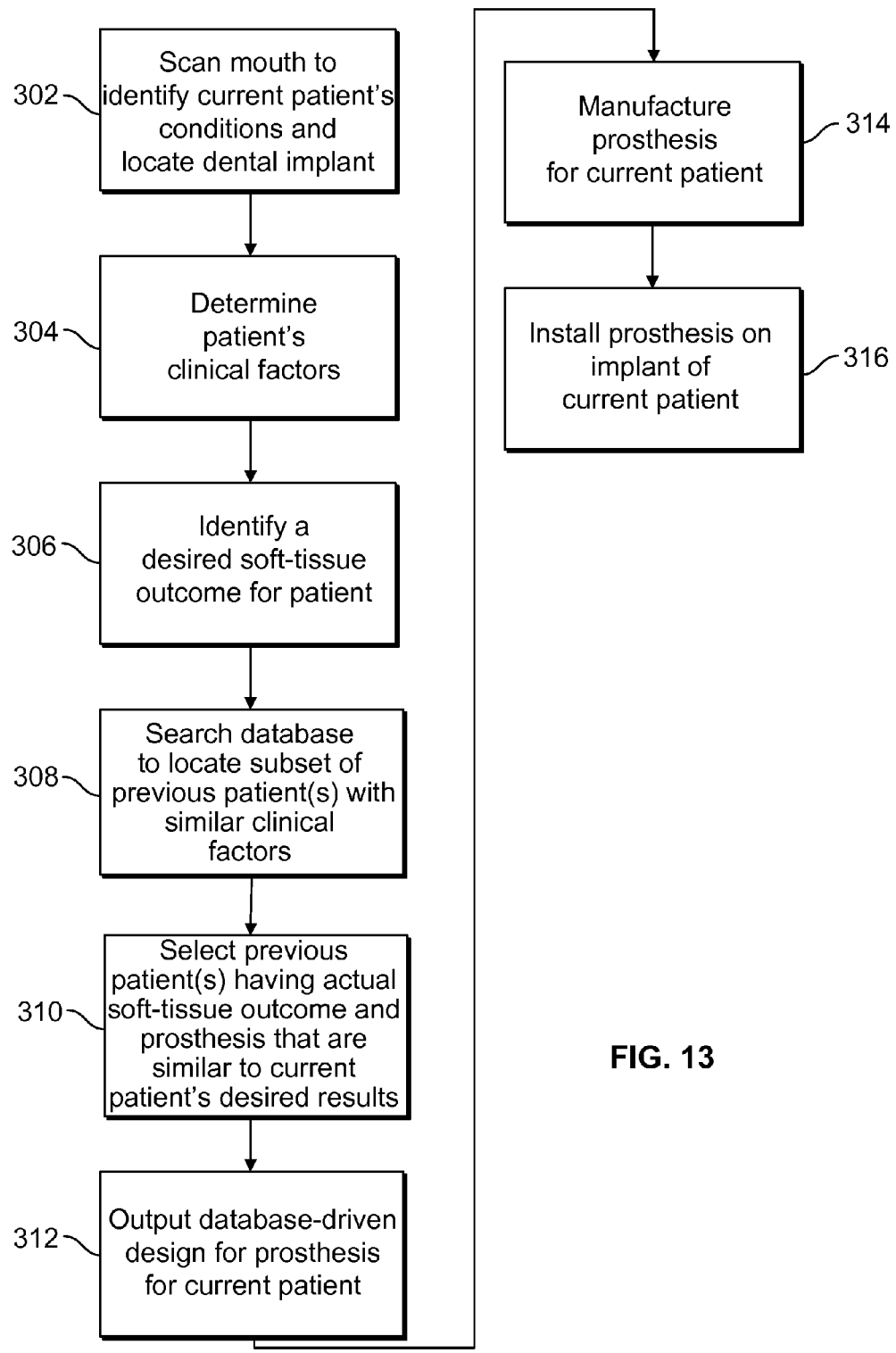
FIG. 13 is a flow chart describing another method of developing a design for the current patient's prosthesis by use of the prosthesis design system of FIG. 2.

FIG. 13 illustrates a flowchart that may be used to develop the database-driven design for the prosthesis for the current patient, such as in Prosthesis Design Example 2. At step 302, the mouth of the patient is scanned to help identify the patient's conditions and locate the dental implant 10. At step 304, a patient's clinical factors are determined and input via a computer input system (usually at the clinical location 48). At step 306, modeling from the scan data is used to identify a desired soft-tissue outcome 32 for the patient, and also an overall shape for the prosthesis (as indicated by the virtual prosthesis 30). At step 308, the information involving the clinical factors is used to search the database 42 to locate previous patients with similar clinical factors.

Based on the searching at step 308, previous patients are selected at step 310 with an actual soft-tissue outcome and prosthesis that are the closest to (i.e., related to) the desired outcome and prosthesis for the current patient. It should be noted that the comparison of the actual prostheses of previous patients to the "shell" of the prosthesis of the current patient (FIG. 1D) may focus primarily (or entirely) on matching sub-gingival aspects (not supra-gingival aspects) because sub-gingival aspects have more of a direct impact or influence on the soft-tissue outcome. Within step 310, one previous patient may be selected that is the closest to the geometry of the actual soft-tissue outcome and prosthesis for the current patient, and a second previous patient may be selected because the prosthesis used by that second previous patient had a more predicted soft-tissue outcome (like Previous Patient Nos. 00389 and 01492 above). At step 312, the features for the prosthesis for the selected previous patients are merged to develop a database driven design for the prosthesis for the current patient. The final design of the prosthesis for the current patient (abutment and crown) can then be sent to the manufacturing facility 49 (or facilities) at step 314. Once the final design has been manufactured, it can be sent to the clinical facility 48 and installed on the implant 10 for the current patient at step 316. And, to build and supplement the database 42, the current patient's soft-tissue outcome is ultimately checked against the desired outcome after installation on the implant 10, such that the current patient becomes a "previous patient" at a later point in time and the prosthesis for the current patient may be used as a baseline design for a similarly situated future patient.

PROSTHESIS DESIGN EXAMPLE 3

This example is similar to Prosthesis Design Example 2 in that additional prosthetic-based clinical factors are analyzed from previous patients to arrive at the final design for the current patient. However, in this example, the geometry of the abutment other previous patients is used to alter a baseline design.

TABLE IV

Search Results for Prosthesis Design Example 3

| | | Prosthetic-Based Clinical Factors | | | Actual Outcome v. Desired Outcome | | |
|---|---|---|---|---|---|---|---|
| Pat. No. | Implant Location | Abutment Material | Abutment Micro-Structure | Implant To Margin (mm) | Predicted Soft-Tissue Contour | Predicted Soft-Tissue Height | Predicted Inter-Papilla Fullness |
| 00004 | Sub-Crestal | ZrO2 | N | 1.8 | Y | N | Y |
| 00012 | Crestal | Ti | N | 1.7 | Y | Y | N |
| 00113 | Crestal | ZrO2 | Y | 2.9 | N | Y | N |
| 00229 | Crestal | Ti | N | 2.5 | Y | N | N |
| 00301 | Sub-Crestal | ZrO2 | Y | 1.6 | Y | N | Y |
| 00389 | Sub-Crestal | ZrO2 | Y | 2.2 | Y | Y | Y |
| 01021 | Crestal | Ti | Y | 1.2 | N | N | Y |
| 01115 | Crestal | ZrO2 | N | 1.9 | Y | N | N |
| 01418 | Crestal | Ti | Y | 1.5 | Y | Y | Y |
| 01492 | Sub-Crestal | ZrO2 | Y | 2.6 | Y | Y | Y |

Figure 15:
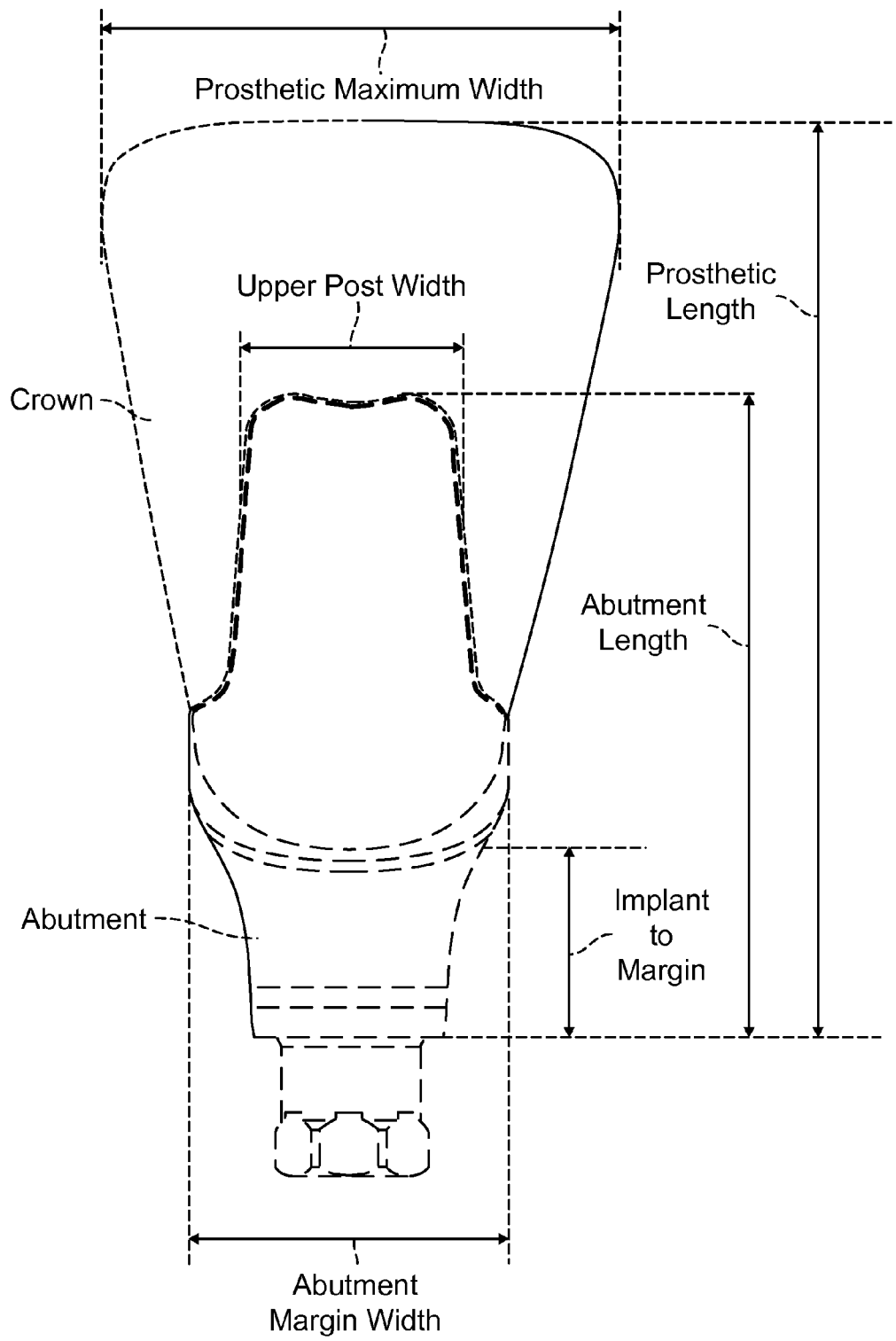
FIG. 15 illustrates a prosthesis with some of the basic geometric design elements.

Table IV is similar to Table III but illustrates how the previous patients' information can be used to alter a geometric design feature, which in this example is the Implant-to-Margin distance (measured from the implant's table to the facial midpoint of the abutment as shown in FIG. 15). In Table IV, the desired outcome and prosthesis for the current patient most closely matches the actual outcome and prosthesis of previous Patient No. 00301. However, for Patient No. 00301, her actual soft-tissue outcome did not exactly match her desired soft-tissue outcome. As noted in the $7^{th}$ column, the Predicted Soft-Tissue Height was not met.

On the other hand, two other previous patients—Patient Nos. 00389 and 01492—may have prosthetic geometries that did not match as well to the current patient's geometry as Patient No. 00301. But, the Predicted Soft-Tissue Contour, Predicted Soft-Tissue Height, and Predicted Inter Papilla Fullness were met in that those two previous patients' desired soft-tissue outcome and their actual soft-tissue outcomes were substantially the same. Thus, an analysis can be conducted by the prosthesis design system 40 to identify a trend or difference (a variable) that may have impacted the different soft-tissue outcomes.

Specifically, for previous Patients Nos. 00389 and 01492, the abutment characteristics were different from Patient No. 00310 in that both had a significantly larger Implant-to-Margin distance (2.2 mm and 2.6 mm) than the Implant-to-Margin distance for Patient No. 00301 (1.6 mm). Because all three abutments have an Abutment Micro-Structure, the prosthesis design system 40 isolates this different variable as being a possible contributing factor to the predictive soft-tissue successes of Patients Nos. 00389 and 01492. For example, perhaps the additional surface area created by the longer length of the Implant-to-Margin distance permitted better connective tissue attachment along the surface of the ZrO2 abutment having the Abutment Micro-Structure.

Accordingly, based on the information from the Previous Patient Nos. 00301, 00389 and 01492, the prosthesis design system 40 automatically develops a design for the current patient's prosthesis. The design has an overall geometry similar to patient No. 00301, except that it increases the Implant-to-Margin distance from 1.6 mm to 2.4 mm (i.e., average between 2.2 mm and 2.6 mm).

Figure 14:
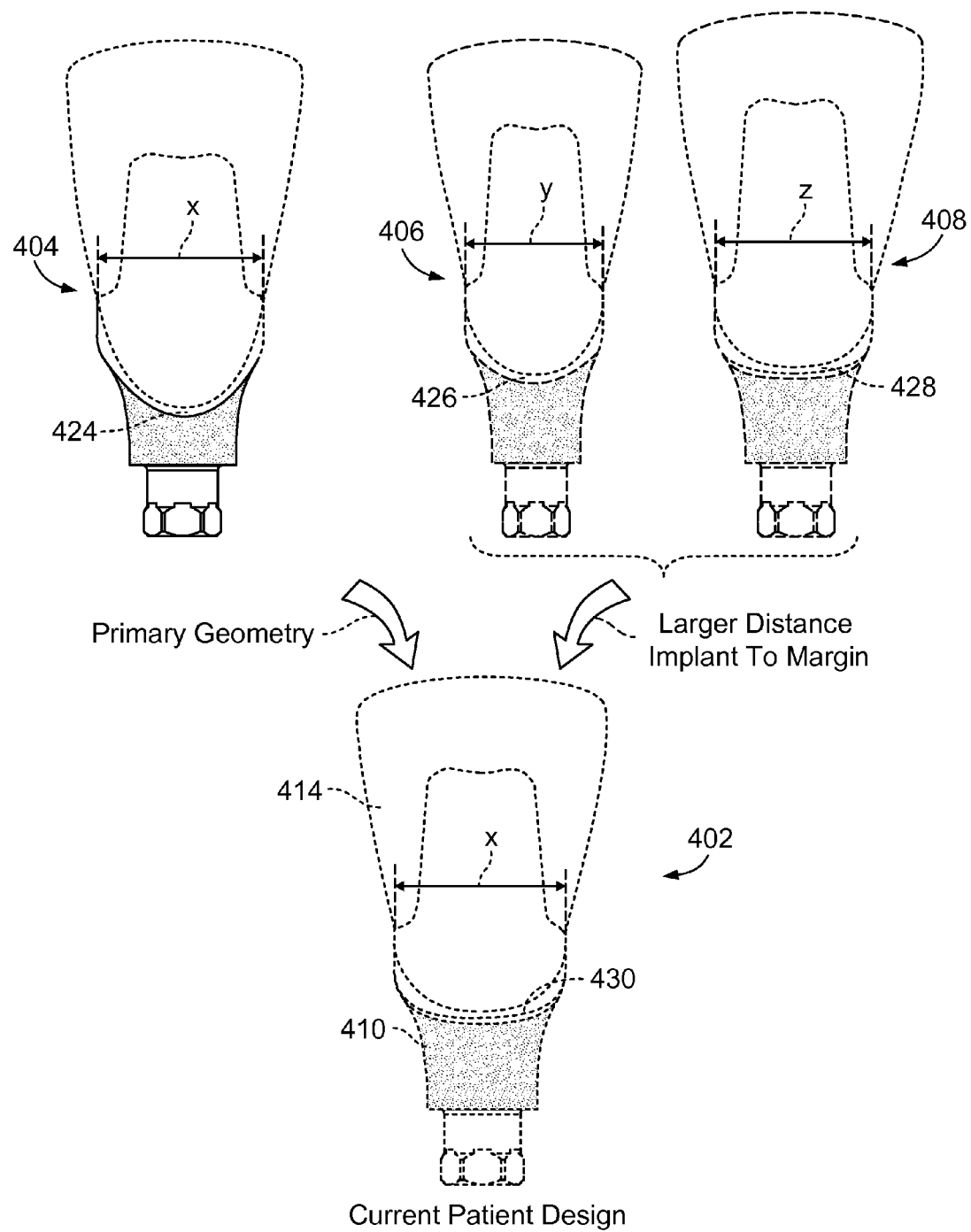
FIG. 14 graphically illustrates the development of another current patient's prosthesis by merging of design features from three prostheses used by three previous patients, as described relative to Table IV.

FIG. 14 graphically illustrates the development of the final design for the current patient's prosthesis 402, which includes an abutment 410 and a crown 414, by merging design features from a prosthesis 404 of Patient No. 00301, a prosthesis 406 of Patient No. 00389, and a prosthesis 408 of Patient No. 01492 in accordance with the design process for Prosthesis Design Example 3. As noted above, Patient No. 00301 lacked an entirely accurate predicted soft-tissue outcome. On the other hand, Patient No. 00389 and Patient No. 01492 had a more accurate predicted soft-tissue outcome. Relative to the abutment for the prosthesis 404, one difference in the designs of the abutment for the prosthesis 406 and the abutment for the prosthesis 408 is that they had a larger implant-to-margin dimension as noted by margins 426 and 428, respectively. In other words, the margin 424 on the abutment associated with the prosthesis 404 of Patient No. 00301 was much closer to the implant.

Accordingly, to design the prosthesis 402 for the current patient, the primary geometry is taken from the prosthesis 404, but a larger dimension exists between the implant and the margin 430 in the abutment 410 (similar to Patient No. 00389 and Patient No. 01492). Other geometrical design features in the abutment 410 and the crown 414 will be substantially more like those same features found in the prosthesis 404 for Patient No. 00301. As just one example, the maximum abutment margin width "X" for the abutment 410 is very similar to the same abutment dimension in the prosthesis 404 used in Patient No. 00301, but is different from those corresponding abutment dimensions "Y" and "Z" for the prosthesis 406 and the prosthesis 408, respectively.

PROSTHESIS DESIGN EXAMPLE 4

This example is similar to Prosthesis Design Example 2 and Example 3 in that additional prosthetic-based clinical factors are analyzed from previous patients to arrive at the final design for the current patient. However, Prosthesis Design Example 4 include developing a final prosthesis for the current patient based on interpolating between two geometries for two prosthesis used onto previous patients, both of whom had accurately predicted soft-tissue outcome. As explained below, Table V below includes prosthetic-based clinical factors that are more focused on a few of the basic geometrical dimensions for the abutment and the crown.

FIG. 15 helps to identify some of the basic dimensions used for prosthesis indicated in Table V. It should, however, be apparent that there are numerous other dimensions (and shapes) for the abutment and the crown that can be measured and stored in the database 42 for each patient as a separate clinical factor. In attempting to locate previous patients with similar geometries for the prosthesis for a particular tooth that is being replaced, it is helpful to know the overall Prosthetic Length, which is measured from the implant-abutment interface. The Prosthetic Length also influences the overall Abutment Length, which is also measured from the implant-abutment interface. The amount of the abutment that engages the soft tissue is the Implant-to-Margin dimension. Considering that the margin typically has a saddle shape, this dimension changes as a function of the circumferential position around a central axis of the abutment. In FIG. 15, it is measured at the midpoint facially (or buccally). However, a similar margin-related dimension can be measured on the lingual side, on the mesial side, and on the distal side, and all of these margin-related dimensions may be stored in the database 42 in association with each previous patient.

FIG. 15 also shows the Prosthetic Maximum Width, which is typically located on an upper region of the crown. The Upper Post Width is measured along the post region of the abutment. And the Abutment Margin Width is measured along the margin of the abutment. Again, other dimensions and shapes for both the crown and the abutment can be stored in association with each previous patient.

00389. And, the final outcome for Patient No. 01492 was also predicted, like Patient No. 00389. However, the desired outcome for the soft tissue location (i.e., the Soft-Tissue Height) for the current patient is not as far down the prosthesis length coronally as the final outcome for Patient No. 01492. This difference in the soft-tissue location may be determined by comparing actual images of Patient Nos. 00389 and 01492 with the desired outcome (e.g., FIG. 1D) of the current patient.

Accordingly, the prosthetic design system 40 adjusts the Implant-to-Margin dimension so as to be between 2.2 mm and 2.6 mm, such as 2.4 mm. In other words, the system interpolates the information for the Implant-to-Margin dimension for Patient Nos. 00389 and 01492 to arrive at the design for the current patient. While the final design for the prosthesis (abutment and crown) for the current patient will be most similar to the previous Patient No. 00389, the Implant-to-Margin dimension for the design will be altered to 2.4 mm (instead of 2.2 mm).

Figure 16:
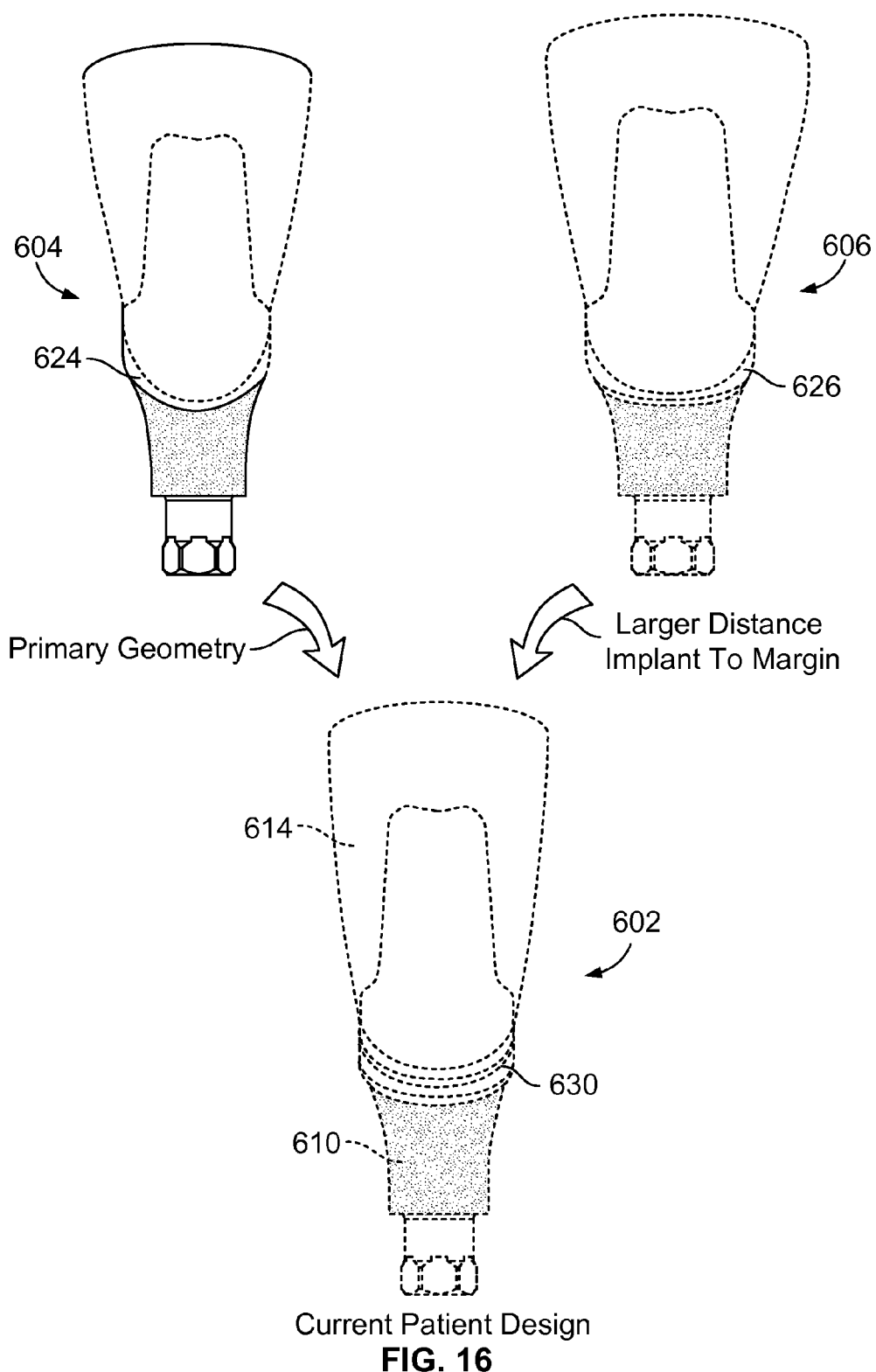
FIG. 16 graphically illustrates the development of yet another current patient's prosthesis by merging of design features from two prostheses used by two previous patients, as described relative to Table V.

FIG. 16 graphically illustrates the development of design for the current patient's prosthesis 602, which includes an abutment 610 and a crown 614, by merging design features from a prosthesis 604 of Patient No. 00389 and a prosthesis 606 of Patient No. 01492 in accordance with the design process for Prosthesis Design Example 4. As noted above in Table V, Patient No. 00389 and Patient No. 01492 both had accurately predicted soft-tissue outcomes. However, the Implant-to-Margin dimension for Patient Nos. 00389, as measured to the margin 624 on the abutment of the pros-

TABLE V

Search Results for Prosthesis Design Example 4.

| | | Prosthetic-Based Clinical Factors | | | Actual Outcome v. Desired Outcome | | |
|---|---|---|---|---|---|---|---|
| Pat. No. | Abutment Material | Prosth. Length (mm) | Abutment Length (mm) | Implant To Margin (mm) | Predicted Soft-Tissue Contour | Predicted Soft-Tissue Height | Predicted Inter-Papilla Fullness |
| 00004 | ZrO2 | 13.25 | 10 | 1.8 | Y | N | Y |
| 00012 | Ti | 11.00 | 7 | 1.7 | Y | Y | N |
| 00113 | ZrO2 | 14.50 | 8 | 2.9 | N | Y | N |
| 00229 | Ti | 12.25 | 9 | 2.5 | Y | N | N |
| 00301 | ZrO2 | 11.75 | 7 | 1.6 | Y | N | Y |
| 00389 | ZrO2 | 12.50 | 7 | 2.2 | Y | Y | Y |
| 01021 | Ti | 10.25 | 6 | 1.2 | N | N | Y |
| 01115 | ZrO2 | 12.00 | 8 | 1.9 | Y | N | N |
| 01418 | Ti | 15.50 | 10 | 1.5 | Y | Y | Y |
| 01492 | ZrO2 | 12.75 | 8 | 2.6 | Y | Y | Y |

Table V is similar to Tables III and IV, but illustrates how the previous patients' information can be used to alter a geometric design feature by interpolation, which in this example is the Implant-to-Margin dimension shown in FIG. 15, which is measured from the implant's table to the facial midpoint of the abutment's margin. In Table V, the desired outcome and prosthesis for the current patient closely matches Patient No. 00389. However, for the current patient, the desired outcome for the soft tissue location (i.e., the Soft-Tissue Height) for the current patient is further down the prosthesis length coronally than the final outcome for Patient No. 00389. Hence, an adjustment is needed. As an example, because tooth #9 is being replaced in the current patient, it may be that the gingival tissue height for the current patient's tooth #8 requires this adjustment to provide a more symmetric appearance.

As indicated in Table V, Patient No. 01492 has a similar sized prosthetic length and abutment length as Patient No.

thesis 604 is too small. On the other hand, the Implant-to-Margin dimension for Patient Nos. 01492, as measured to the margin 626 on the abutment of the prosthesis 606 is too large for the current patient.

Accordingly, to design the prosthesis 602 for the current patient, the primary geometry is taken from the prosthesis 604. But, a different dimension is chosen for the Implant-to-Margin dimension that is between the corresponding dimensions for the prosthesis 604 (2.2 mm) and the prosthesis 606 (2.6 mm).

Consequently, the Prosthesis Design Examples 2, 3, and 4 illustrate how dimensional changes and material changes can be made to the prosthesis based on information that is stored in the database 42 for multiple previous patients. In each of these examples, the prosthetic design system 40 is used to locate previous patients with (i) similar clinical factors as the current patient and (ii) similar prosthetic-based clinical factors. Additionally information about the previous patients' soft-tissue outcomes (both the actual soft-tissue outcomes, and differences in the accuracies of the previous patients' soft-tissue outcomes) may also be used to develop a final design for the prosthesis for the current patient.

Furthermore, in the Prosthesis Design Examples 2, 3, and 4, the methodology has been described as being more automated in that the prosthesis design system 40 performs all of the tasks/steps (or nearly all of the task/steps) needed to arrive at the final design for the current patient. However, it should be understood that the methodology can include additional manual steps by an operator at the clinical location 48, the design facility 50, and/or the prosthetic manufacturing facility 49. As an example, the prosthetic design system 40 could identify to an operator that the actual soft tissue outcome for Patient No. 00004 was not as predicted. The prosthetic design system 40 could then be prompted by the operator to identify other similarly situated previous patients that had predicted soft-tissue outcomes and any potential geometric or material differences in those previous patients that may have led to the predicted soft-tissue outcome. After identifying these previous patients and displaying them on a computer display to the operator, the operator may be able to select whether to implement the geometric difference or the material difference in developing the final design of the prosthesis for the current patient.

In the previous Prosthesis Design Examples 1, 2, 3, and 4, the initial scan of the current patient's mouth occurs after the placement of the implant, capturing the image of the soft tissue after the implant surgery. While not discussed previously, the prosthetic design system 40 could be implemented to dictate the exact healing abutment (width, height, and emergence profile) to be chosen for the patient after stage-one osseointegration has occurred. In other words, in the Prosthesis Design Examples 1, 2, 3, and 4, each previous patient may have information about the details of the healing abutment stored in the database 42 (like the information on the abutment and prosthesis) and the current patient would receive a recommendation for the healing abutment to be used prior to the prosthesis, which is another aspect of the patient's design that would be performed by the prosthetic design system 40. The healing abutment would begin developing the soft-tissue contours and shapes into which the custom prosthesis will eventually be placed when it is attached to the implant. And, because some procedures may call for the use of a temporary prosthesis in stage-two surgery (instead of a healing abutment), data for a temporary prosthesis can also be stored in the database 42 in lieu of or in addition to the healing-abutment data.

As yet a further alternative, the initial scan of the current patient's mouth could occur after a stage-two healing of the soft tissue such that the soft tissue is in a more final and healed condition. That could be one of the scans (or the only scan) used for developing the model that dictates the desired soft-tissue outcome for the current patient.

While the present invention has been described relative to the development of a design for a prosthesis to be mounted on a dental implant that has already been installed in the patient's mouth, the present invention contemplates a design system 40 in which the overall surgical process, including the selection and installation of the dental implant, can be based upon information from previous patients. In this embodiment, initial scan(s) of the patient would include the details of the underlying bone structure (likely through a CT scan) and the soft tissue, and the current patient's model (FIG. 1D) would be developed based on that scan data. The design system 40 would then search for previous patients having (i) a similar bone conditions and soft-tissue conditions and (ii) a soft-tissue outcome and a prosthetic shape that are similar to the current patient's desired soft-tissue outcome and prosthetic shape. The database would then dictate the type, size, and/or shape of the implant to be installed, and the location (depth and angular orientation) for installation of the implant. A common surgical guide could be then designed to ensure the appropriate installation of the implant at the database-dictated location. Such as surgical guide is described in U.S. Publication No. 2011/0306008, which is hereby incorporated by reference in its entirety. Thus, an implant, a surgical guide, a healing abutment, and/or the prosthetic design would be output from the design system 40. Or, after implant installation (or healing abutment placement), a secondary scan could be taken to perform the prosthetic design in the manner described above. In short, the same type of processes described above can be used to dictate the design for the implant and its placement (in addition to the prosthesis design and/or selection of the healing abutment or temporary abutment). Once a final design for the current patient's prosthesis is achieved, the final design for the prosthesis can then be used to manufacture the prosthesis as described previously, and the manufactured prosthesis can be mounted on the dental implant at some point in time after the implant has been installed in the patient's mouth.

The present invention contemplates that, over a significant period of time, the predictability of a current patient's soft tissue outcome should become more accurate because the database 42 will be using information for a current patient's design that is based on previous patients who have achieved predictable and successful soft-tissue results. Accordingly, as time progresses, there should be an increase in the percentage of previous patients stored in the database 42 who have positive and predictable soft-tissue outcomes. In summary, the positive soft-tissue results achieved by patients should continue to increase over a period of time.

While the present disclosure primarily discusses the entire "shell" being matched, the "shell" can be divided into the sub-gingival aspect and supra-gingival aspect (or a lower portion and upper portion), as described above. The sub-gingival aspect has the most direct impact on the resultant gingival contours and, therefore, is most relevant in terms of predictive modeling. While it might be desirous to match the entire shell so as to minimize the amount of design work/input required by the operator, it should be noted that the matching can be primarily (or totally) focused on matching the sub-gingival aspects. There is oftentimes little (if any) "prediction" necessary with the supra-gingival aspect of the prosthetic design because nothing is being displaced and/or contoured with the supra-gingival geometry (i.e., what you see if what you get). To make the predictive model more efficient and robust, the present invention contemplates a prosthetic design system 40 primarily (or totally) matching the sub-gingival geometries of the prosthesis (and soft-tissue outcomes) between the current patient and previous patients. Once this is matched, the supra-gingival geometry can be developed in the computer (or with some operator assistance) to match the supra-gingival aspect of the current patient's "shell" design and will appear the same once installed.

Further, it should be noted that the present invention can be used to alter the design for a current patient's prosthesis that has already been substantially designed (as opposed to be being simply a "shell"). For example, a more finalized design for a current patient's prosthesis may include details for an abutment and/or a crown. The more finalized design (and possibly the desired soft-tissue outcome) can then be compared against the information for previous patients in the database 42 to identify previous patient(s) that had predictable actual soft-tissue outcomes. Based on those identified previous patient(s), the more finalized design can be altered to include design features corresponding to the identified previous patient(s) that may help to achieve a predicable soft-tissue outcome for the current patient.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present invention, which is set forth in the claims that follow.

What is claimed is:

1. A method of designing a patient-specific prosthesis for a current patient, comprising:
  receiving scan data including information on a location of a dental implant installed in the current patient's mouth below the patient's soft tissue to identify conditions at a location at which the patient-specific prosthesis is to be placed on the dental implant;
  identifying a desired soft-tissue outcome for the current patient's soft tissue at the location of the dental implant;
  determining a plurality of clinical factors for the current patient that relate to the desired soft-tissue outcome for the patient;
  accessing a database having soft-tissue-outcome information for each of a plurality of previous patients who underwent an operation in which a dental prosthesis was implanted in the previous patients' mouth, the soft-tissue outcome information including information on soft-tissue contour, soft-tissue height, and/or soft-tissue inter-papillae fullness for each of the plurality of previous patients, wherein the database further includes clinical-factor information for each of the plurality of previous patients;
  displaying, on a display device, a virtual model of the patient's mouth based on the scan data, the virtual model including the dental implant;
  based on the soft-tissue-outcome information and the clinical-factor information for at least a first of the plurality of previous patients, developing a design for the patient-specific prosthesis for the current patient that includes design features from the dental prosthesis used by the first previous patient, wherein the clinical-factor information for the first previous patient correlates to at least some of the plurality of clinical factors for the current patient; and
  displaying, on the display device, the design of the patient-specific prosthesis in conjunction with the virtual model of the patient's mouth, wherein the soft-tissue outcome information for the plurality of previous patients includes predicted or desired soft-tissue outcome information and actual soft-tissue outcome information.

2. The method of claim 1, wherein the plurality of clinical factors for the current patient are selected from the group consisting of bone-tissue type, replaced-tooth location, implant-placement location, loading timeframe, age, sex, race, and soft-tissue displacement.

3. The method of claim 1, wherein the desired soft-tissue outcome includes a desired contour for soft tissue that is to reside adjacent to the patient-specific prosthesis.

4. The method of claim 1, wherein the identified conditions include a soft-tissue condition after soft tissue has healed around a healing abutment attached to the dental implant.

5. The method of claim 1, wherein the identified conditions include a soft-tissue condition around the dental implant.

6. The method of claim 1, wherein the plurality of clinical factors are three clinical factors, the three clinical factors including a replaced-tooth number, age, and sex, and wherein the plurality of previous patients includes the first previous patient and a second previous patient, the design for the patient-specific prosthesis for the current patient being based in part on a combination of the dental prostheses used in the first previous patient and the second previous patient, respectively.

7. The method of claim 1, wherein developing the design for the patient-specific prosthesis occurs by automatically developing a subgingival portion that is based on the dental prosthesis used by the first previous patient.

8. The method of claim 1, wherein the plurality of previous patients includes the first previous patient and a second previous patient, the dental prosthesis used for the first patient being a baseline design used in designing the patient-specific prosthesis for the current patient, and at least one design element from the dental prosthesis for the second patient is used to influence or alter a corresponding design element of the baseline design of the patient-specific prosthesis.

9. The method of claim 8, wherein the corresponding design element is a dimension of an abutment that is a part of the patient-specific prosthesis.

10. The method of claim 8, wherein the corresponding design element is a material or surface characteristic of an abutment that is a part of the patient-specific prosthesis.

11. The method of claim 8, wherein the soft-tissue-outcome information for the second patient includes information indicating a substantial matching of predicted and actual soft-tissue conditions for the second patient.

12. The method of claim 8, wherein developing the design for the patient-specific prosthesis for the current patient includes altering the design for the patient-specific prosthesis through operator inputs to a computer system coupled to the display device.

13. The method of claim 8, wherein identifying the desired soft-tissue outcome for the current patient includes (i) developing, by use of the virtual model of the mouth of the current patient, a desired soft-tissue height and a desired soft-tissue contour, and (ii) displaying, on the display device coupled to the computer system, the desired soft-tissue height and the desired soft-tissue contour.

14. The method of claim 13, wherein developing the design for the patient-specific prosthesis for the current patient is accomplished automatically through the computer system.

15. The method of claim 1, wherein developing the design for the patient-specific prosthesis for the current patient is further based on a virtual prosthesis model for the current patient being similar to the dental prosthesis for the first patient, information on the dental prosthesis for the first patient being stored in the database.

16. The method of claim 15, further including comparing a subgingival portion of the virtual prosthesis model to a subgingival portion of the dental prosthesis of the first patient.

17. The method of claim 1, further including selecting the at least first previous patient from the plurality of previous patients by (i) comparing the clinical factors of the current patient to the clinical-factor information of the plurality of previous patients, and (ii) comparing the desired soft-tissue outcome of the current patient to the soft-tissue outcome information of the plurality of previous patients.

18. The method of claim 17, wherein the design features are from the subgingival portions of an abutment used by the first patient, the abutment being a part of the dental prosthesis used by the first patient.

19. The method of claim 1, wherein the soft-tissue outcome information for the plurality of previous patients includes image data related to the previous patients' soft-tissue outcome.

20. The method of claim 1, further comprising correlating the soft-tissue outcome information of the first patient with the desired soft-tissue outcome for the current patient, the correlating step establishing that the soft-tissue outcome information of the first patient is similar to the desired soft-tissue outcome for the current patient.

* * * * *

UNITED STATES PATENT AND TRADEMARK OFFICE
CERTIFICATE OF CORRECTION

PATENT NO. : 9,839,496 B2  
APPLICATION NO. : 13/770921  
DATED : December 12, 2017  
INVENTOR(S) : Herrington et al.

Page 1 of 1

It is certified that error appears in the above-identified patent and that said Letters Patent is hereby corrected as shown below:

On the Title Page

On page 3, in Column 2, under "Other Publications", Line 2, delete "Arp." and insert --Apr.-- therefor Signed and Sealed this  
Twenty-sixth Day of March, 2019

Andrei Iancu  
*Director of the United States Patent and Trademark Office*